United States Patent
Matsuyama

[11] Patent Number: 5,892,985
[45] Date of Patent: Apr. 6, 1999

[54] EYE BALL DETECTING DEVICE

[75] Inventor: Shinichi Matsuyama, Tokyo, Japan

[73] Assignee: Canon Kabushiki Kaisha, Tokyo, Japan

[21] Appl. No.: 502,525

[22] Filed: Jul. 14, 1995

[30] Foreign Application Priority Data

Jul. 15, 1994 [JP] Japan ..................................... 6-163777

[51] Int. Cl.⁶ .............................. A61B 3/14; G03B 17/00
[52] U.S. Cl. .................................. 396/18; 396/51; 348/78
[58] Field of Search ................................... 354/402, 432, 354/474, 478, 479, 195.1, 209, 62; 396/51, 18; 348/78

[56] References Cited

U.S. PATENT DOCUMENTS

| | | | |
|---|---|---|---|
| 5,138,354 | 8/1992 | Okada et al. ........................... | 354/400 |
| 5,200,774 | 4/1993 | Nakajima ................................. | 354/62 |
| 5,486,892 | 1/1996 | Suzuki et al. ........................... | 354/402 |
| 5,537,181 | 7/1996 | Owashi et al. .......................... | 354/410 |
| 5,541,400 | 7/1996 | Hagiwara et al. .................. | 250/208.1 |
| 5,585,884 | 12/1996 | Onuki ....................................... | 396/51 |

FOREIGN PATENT DOCUMENTS 3192338  8/1991  Japan .

*Primary Examiner*—Safet Metjahic
*Assistant Examiner*—Christopher E. Mahoney
*Attorney, Agent, or Firm*—Fitzpatrick, Cella, Harper & Scinto

[57] ABSTRACT

An eye ball detecting device includes a light-receiving unit on which a plurality of regions each including of a plurality of pixels are set, and which receives a reflected image from an eye ball of a user or a person to be examined, Furthermore, the device includes a determination unit for determining the approach of the eye ball of the user to the device when the output from the light-receiving unit satisfies a predetermined condition. The light-receiving unit outputs only one luminance value for each region.

10 Claims, 18 Drawing Sheets

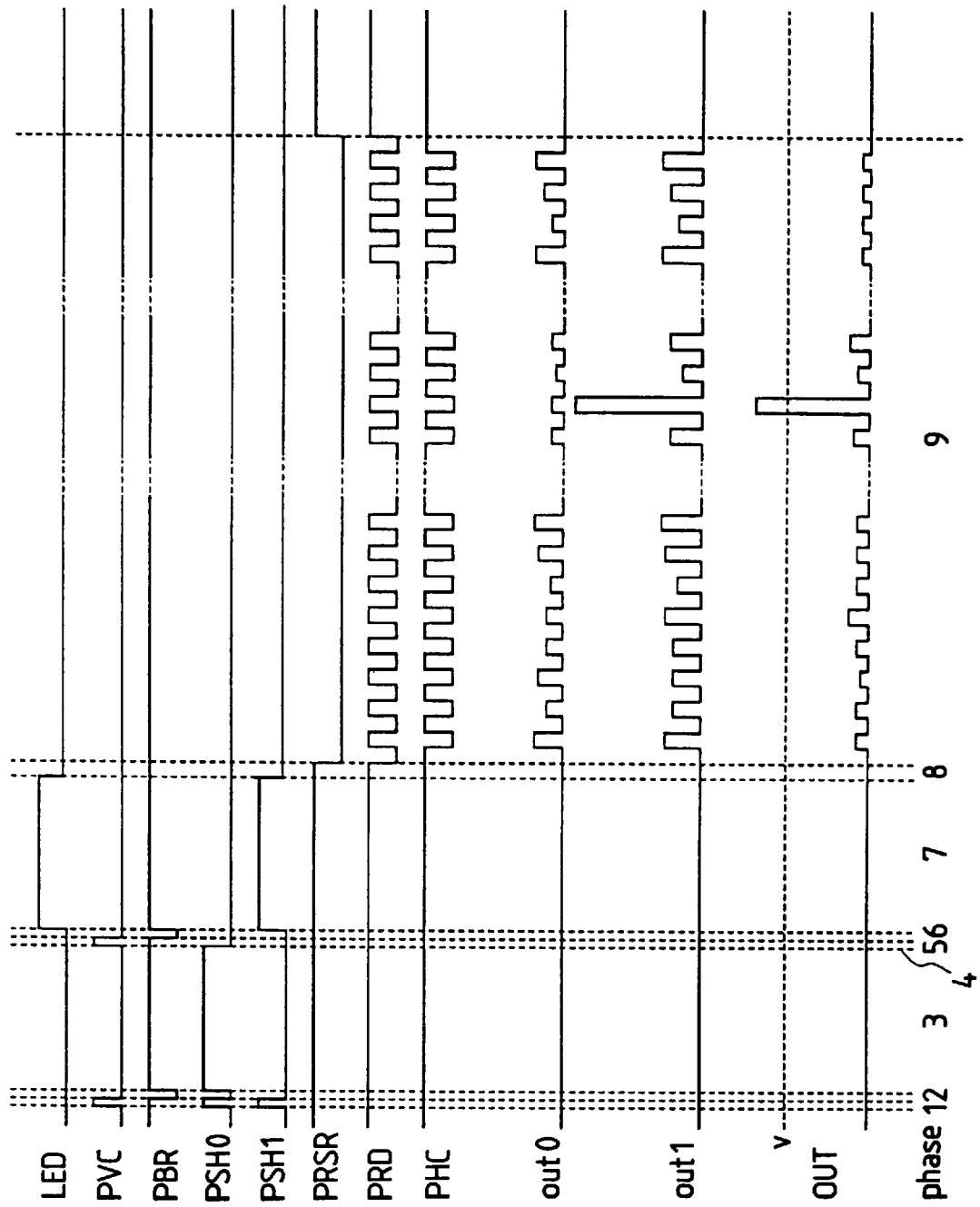

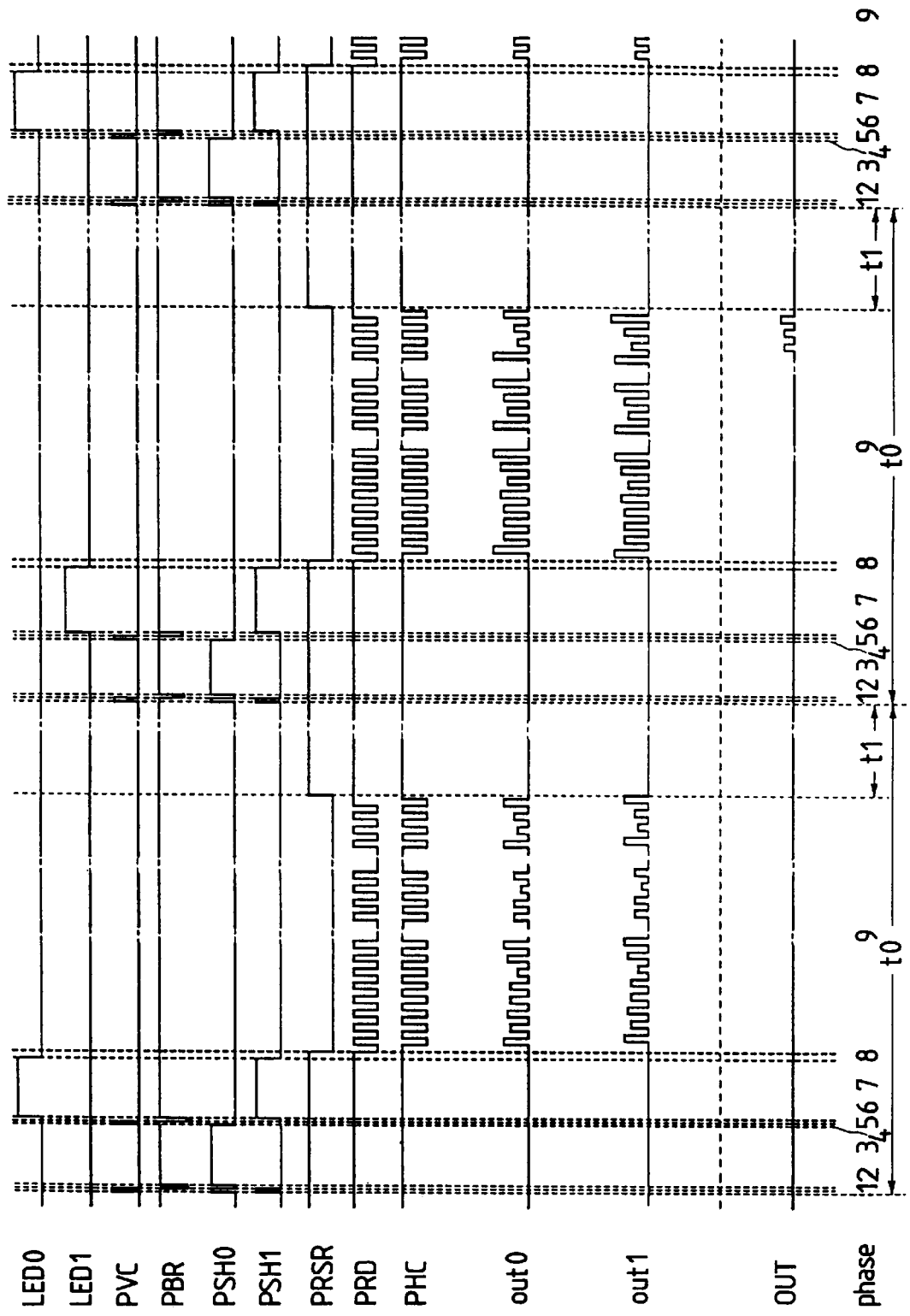

EYE BALL DETECTING DEVICE

BACKGROUND OF THE INVENTION

1. Field of the Invention

The present invention relates to an eye ball detecting device which can detect the presence/absence of an observer's eye and, more particularly, to an eye ball detecting apparatus which detects the presence/absence of an observer's eye on the basis of an eye ball image.

2. Related Background Art

Conventionally, U.S. Pat. No. 5,138,354 discloses a camera which uses a switch arranged in the grip portion of the camera, and a light-emitting element and a light-receiving element arranged in the finder portion, and turns on the switch in the grip portion when a user holds a camera to look into a finder. On the other hand, U.S. Pat. No. 5,200,774 discloses a camera which can detect the approach of a user's face to a finder by utilizing a technique for detecting the approach of an object by receiving light emitted from a light-emitting element and reflected by the object. Also, Japanese Laid-Open Patent Application No. 3-192338 filed by the present applicant discloses an observation apparatus which can discriminate, based on a received image signal, if an approaching object is an eye ball.

However, in the cameras disclosed in U.S. Pat. Nos. 5,138,354 and 5,200,774 as the prior art, the grip switch cannot be correctly operated depending on the holding state of the camera, and the grip shape is considerably limited so as to reliably operate the grip switch.

On the other hand, since the approach or proximity detection technique for detecting the presence/absence of light reflected by an object responds to any object present near the finder, operation errors often occur in response to an object other than the eye ball.

In the eye ball detection technique which is disclosed in Japanese Laid-Open Pat. Application No. 3-192338 and can detect the eye ball on the basis of a received image, whether or not an approaching object is an eye ball can be discriminated based on an image signal, and operation errors can be eliminated. However, in order to obtain a detection result by processing an image obtained by an area sensor, a large-capacity memory for storing the data of a large number of two-dimensionally distributed pixels, and calculation means for calculating data at high speed are required. The consumption power of the calculation means becomes inevitably large.

SUMMARY OF THE INVENTION

One aspect of this invention is to provide an eye ball detecting device which comprises light-receiving means having a light-receiving element which is set with a plurality of regions each defined by a plurality of pixels, and receives a reflected image from an eye ball of a user or a person to be examined, and discrimination means for, when an output from the light-receiving means satisfies a predetermined condition, determining the approach of the eye ball of the user or the person to be examined, wherein since the light-receiving means outputs one luminance value for each of the regions, the approach of the eye ball can be detected at high speed, and the consumption of power can be reduced.

BRIEF DESCRIPTION OF THE DRAWINGS

FIG. 7 is a timing chart showing the operation of the first embodiment (when an eye is detected);

FIG. 8 is a timing chart showing the operation of the first embodiment (when an eye is not detected);

DESCRIPTION OF THE PREFERRED EMBODIMENTS

Figure 1:
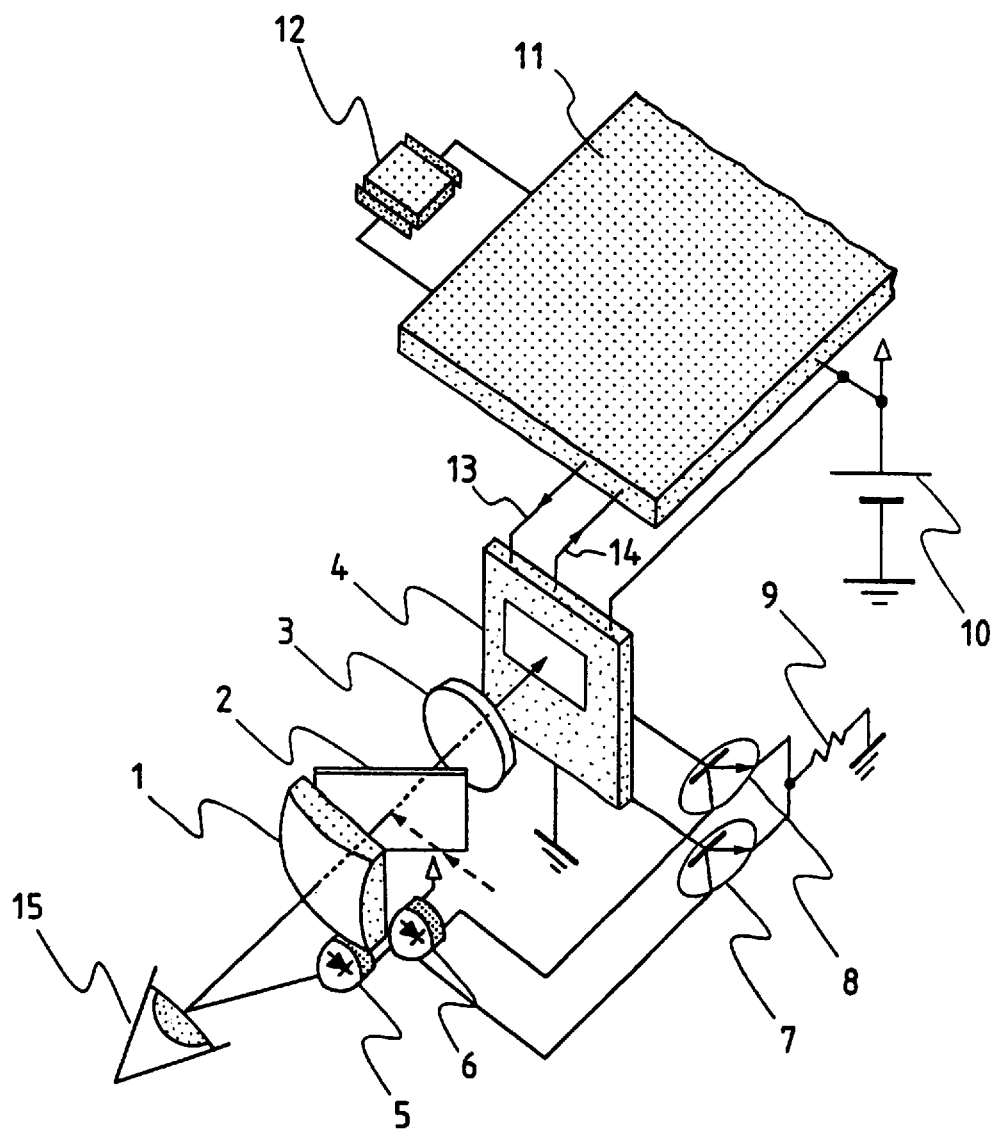
FIG. 1 is a schematic view showing an eye ball detecting device for a camera according to the first embodiment of the present invention.

FIG. 1 shows an eye ball detecting device according to an embodiment of the present invention. Referring to FIG. 1, the device includes a finder eyepiece lens 1 of a camera, a dichroic mirror 2 for separating infrared light as light including signal light from the finder side and a finder light beam as visible light from the object field, an imaging lens 3 for forming an image of an eye, that looks into the finder, on an area sensor IC 4, the area sensor IC 4 having a light-receiving sensor unit for forming an image signal by photoelectrically converting the image. The device also includes infrared light-emitting diodes 5 and 6 which serve as light sources for illuminating the eye that looks into the finder, and are disposed at different positions. The device further includes transistors 7 and 8 for respectively driving the infrared light-emitting diodes 5 and 6 in accordance with driving signals from the area sensor IC, a resistor 9 for suppressing the driving currents of the infrared light-emitting diodes 5 and 6, a battery 10 serving as a power supply, a camera control circuit 11, an oscillator 12 for generating operation clocks, an operation clock signal line 13, and an eye ball detection signal line 14. In FIG. 1, an eye 15 of an observer approaches the finder.

Figure 2:
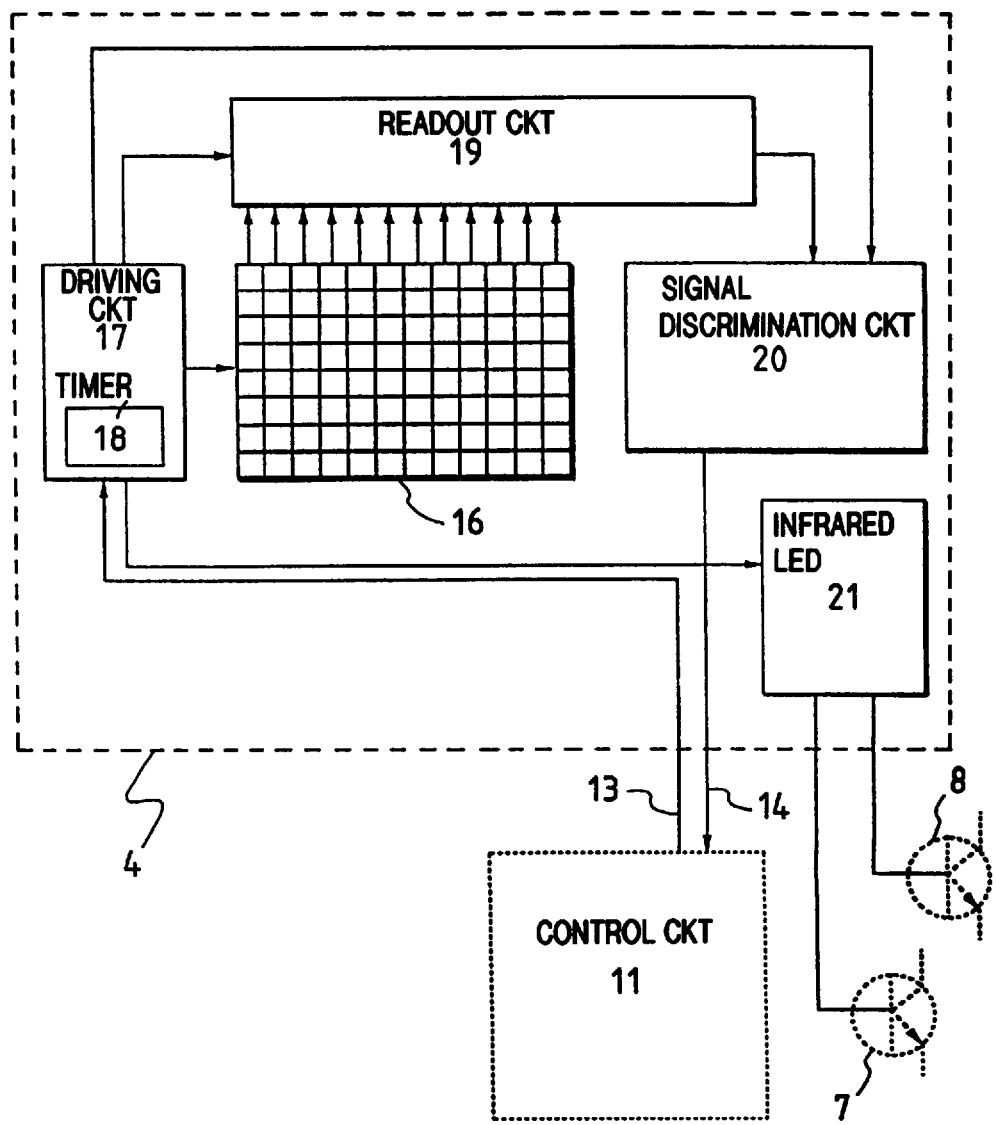
FIG. 2 is a block diagram of a sensor IC 4 shown in FIG. 1.

FIG. 2 shows the arrangement of the area sensor IC 4 in the eye ball detecting device for the camera shown in FIG. 1. The area sensor IC 4 is constituted by components 16 to 21, and is connected to the components 7, 8, 11, 13, and 14 shown in FIG. 1.

Referring to FIG. 2, an area sensor unit 16 in the area sensor IC 4 serves as a light-receiving sensor constituted by a large number of pixels. A sensor driving circuit 17 performs accumulation control and readout control of the area sensor unit 16, and incorporates a timer 18 for measuring a time interval for repetitive operations. A readout circuit 19 sequentially reads out image signals from the area sensor unit 16 in response to timing signals from the sensor driving circuit 17, and supplies the readout signals to a signal discrimination circuit 20. The signal discrimination circuit 20 discriminates, based on the image signals from the readout circuit 19, if the eye approaches the finder. An infrared light-emitting diode driving circuit 21 turns on the infrared light-emitting diode 5 or 6 via the transistor 7 or 8 in synchronism with the driving timing of the sensor driving circuit.

Figure 3:
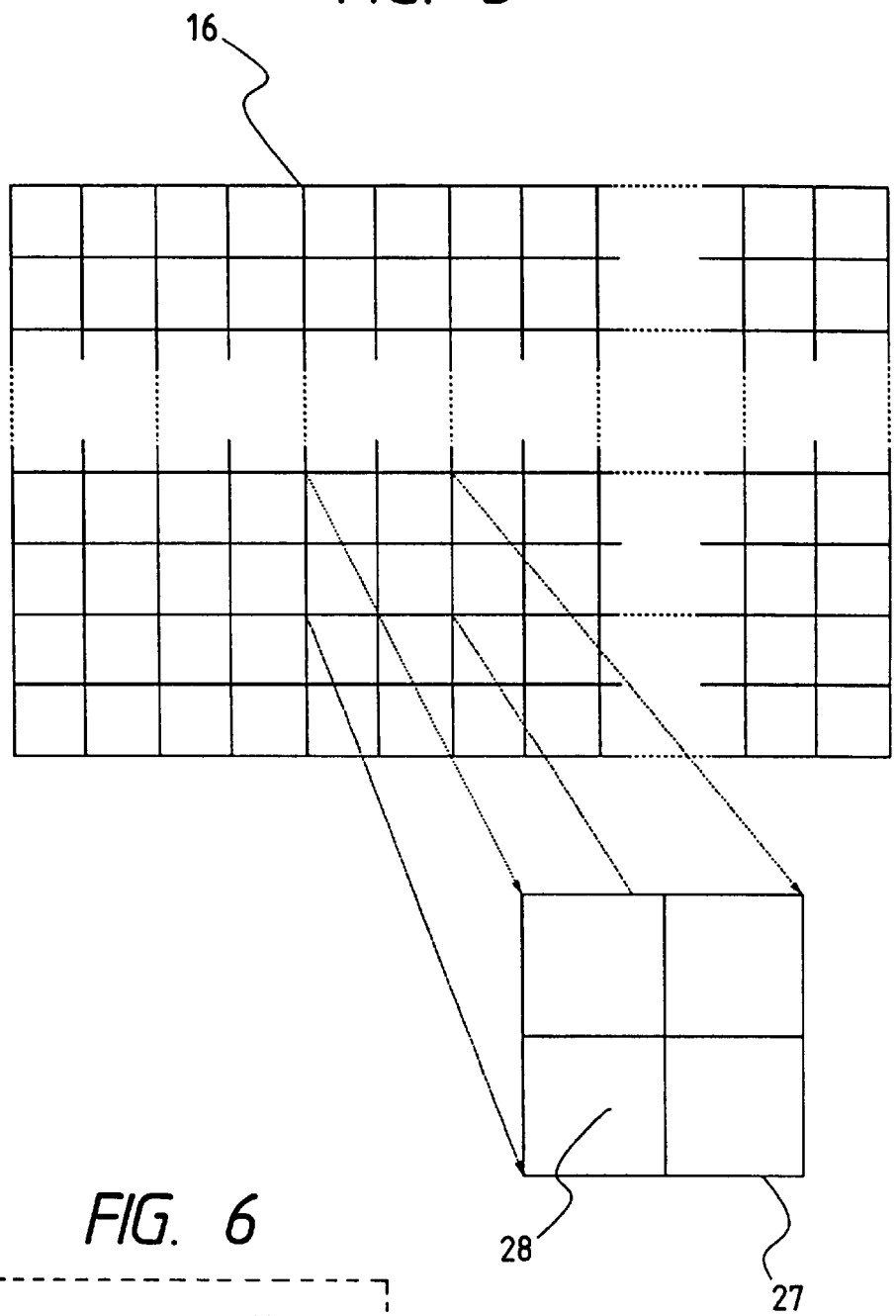
FIG. 3 is a view showing the relationship between the pixels and blocks on an area sensor unit 16 in FIG. 2.

FIG. 3 shows divided blocks obtained by dividing the screen surface of the area sensor unit 16. Each block is defined by a total of four pixels, i.e., has a two-pel vertical size, and a two-pel horizontal size.

Figure 4:
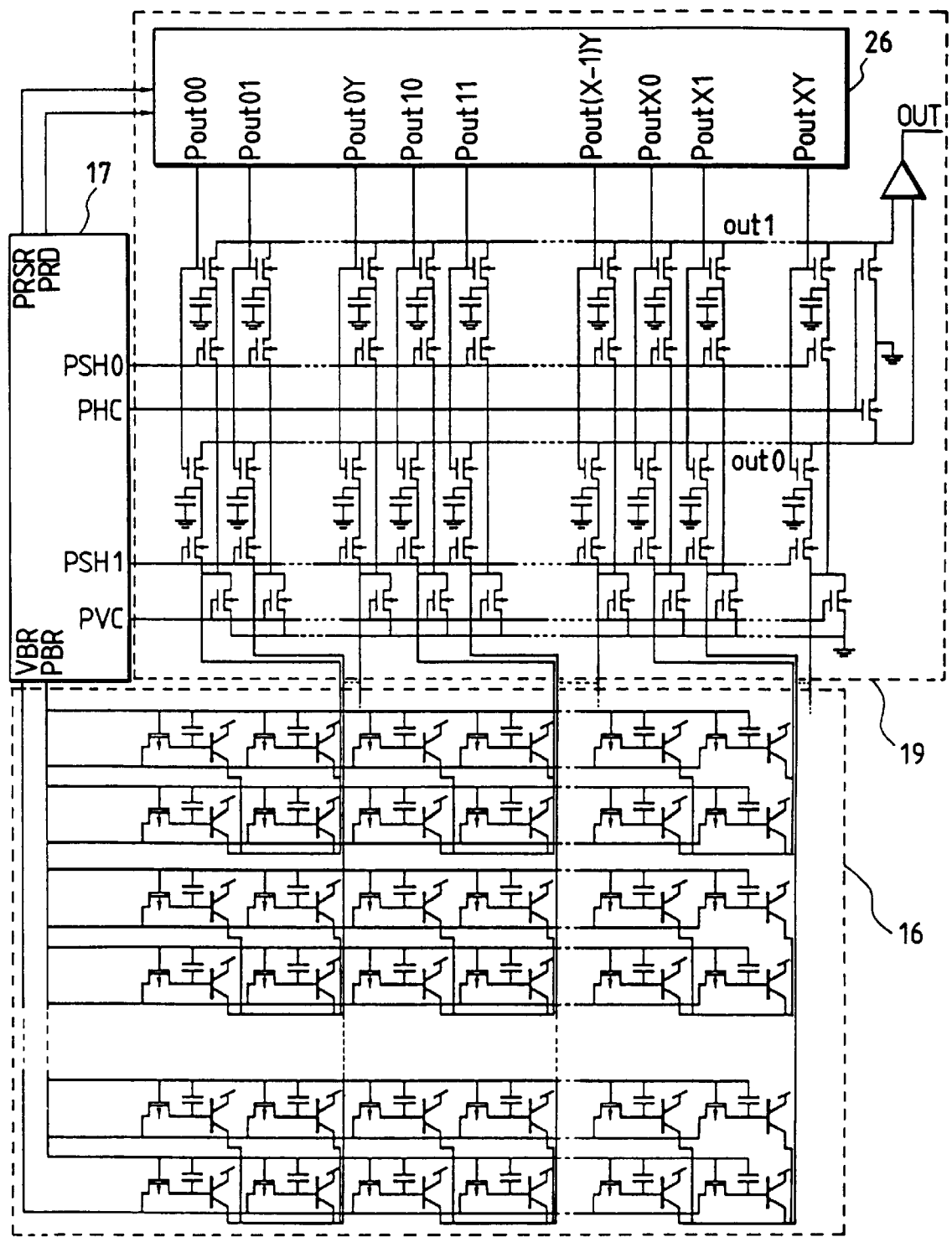
FIG. 4 is a circuit diagram showing the arrangement of the area sensor unit 16 and a readout circuit 19 shown in FIG. 2 when an area sensor is constituted by a nondestructive readout photoelectric conversion element.

FIG. 4 shows the arrangement of the area sensor unit and the readout circuit when the area sensor is constituted by a nondestructive readout photoelectric conversion element.

Referring to FIG. 4, a nondestructive readout photoelectric conversion element driving circuit 17 corresponds to the sensor driving circuit 17 in FIG. 2. A nondestructive readout photoelectric conversion element sensor unit 16 corresponds to the area sensor unit 16 in FIG. 2. A readout circuit 19 corresponds to the circuit 19 in FIG. 2. The readout circuit 19 includes a shift register 26 for sequentially supplying the readout timings of the respective blocks.

Figure 5:
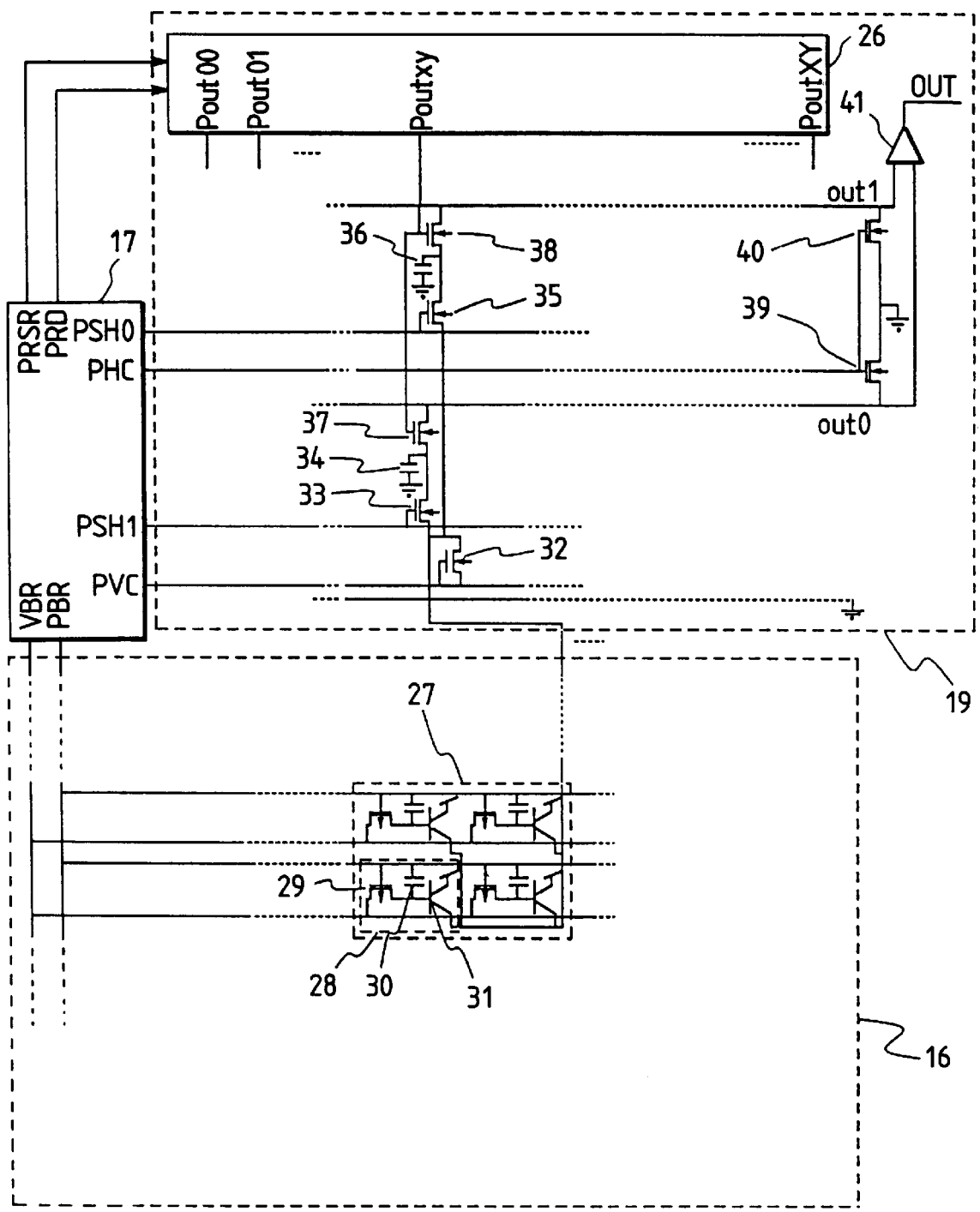
FIG. 5 is a partial circuit diagram showing the arrangement for one block to explain the sensor arrangement shown in FIG. 4 and its operation for the sake of convenience.

FIG. 5 is a partial circuit diagram showing the arrangement for one block to explain the sensor arrangement shown in FIG. 4 and its operation for the sake of convenience.

Referring to FIG. 5, components 17, 16, 19, and 26 respectively correspond to those in FIG. 4. A block 27 consists of a plurality of pixels (in this embodiment, four pixels), and a cell 28 constitutes one pixel of an image sensor. The cell 28 includes a MOS transistor 29 which serves as switch means for resetting the base potential of a transistor 31 in accordance with a base reset signal PBR supplied from the driving circuit 17, a sensor capacitor 30, and the NPN transistor 31. The transistor 31 serves as a sensor portion of the nondestructive readout photoelectric conversion element. More specifically, the base (or a portion connected to the base) of the transistor 31 serves as a photosensitive portion and a signal accumulation portion, and the transistor 31 outputs, from its emitter, a voltage according to a base potential corresponding to the charge amount accumulated or built up on its base. The outputs (emitter outputs) from the pixels constituting each block are commonly supplied to the readout circuit 19 as an output from the block. The readout circuit 19 includes a MOS transistor 32 serving as switch means for resetting the block output to the ground potential in accordance with an emitter reset signal PVC supplied from the driving circuit, a MOS transistor 33 serving as switch means for supplying the block output to a sample & hold capacitor 34 in accordance with a sample & hold signal PSH1 supplied from the driving circuit 17, the sample & hold capacitor 34 for sampling and holding the block output, a MOS transistor 35 serving as switch means for supplying the block output to a sample & hold capacitor 36 in accordance with a sample & hold signal PSH0 supplied from the driving circuit 17, the sample & hold capacitor 36 for sampling and holding the block output, a MOS transistor 37 serving as switch means for outputting a signal, which is sampled and held by the capacitor 34 in accordance with the sample & hold signal PSH0, onto an output line out0 in accordance with an output signal Pout xy for each block supplied from the shift register 26, a MOS transistor 38 serving as switch means for outputting a signal, which is sampled and held by the capacitor 36 in accordance with the sample & hold signal PSH1, onto an output line out1 in accordance with an output signal Pout xy for each block supplied from the shift register, MOS transistors 39 and 40 serving as switch means for respectively resetting the output lines out0 and out1 to the ground potential in accordance with a reset signal PHC supplied from the driving circuit 17, and an operator 41 for outputting the difference between the signals on the output lines out0 and out1 to a terminal OUT.

Components 32 to 38 or equivalents are arranged in correspondence with block outputs, and constitute the same circuits as those constituted by the components 32 to 38. These components are also connected to the driving circuit 17, the shift register 26, and the output lines out0 and out1, and constitute the readout circuit 19 together with the shift registers 26, the MOS transistors 39 and 40, and the operator 41.

Figure 6:
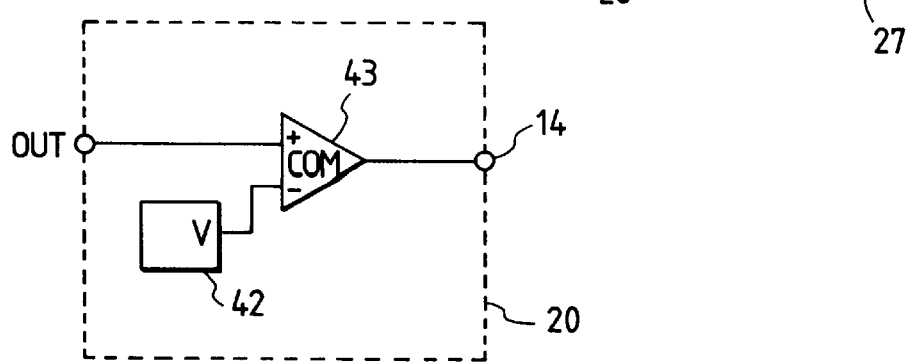
FIG. 6 is a circuit diagram showing the arrangement of a signal discrimination circuit 20 shown in FIG. 2.

FIG. 6 shows the arrangement of the signal discrimination circuit 20 shown in FIG. 2. Referring to FIG. 6, a constant voltage circuit 42 generates a predetermined comparison level v. A comparator 43 compares the output signal from the readout circuit 19, i.e., the output OUT from the operator 41 with the comparison level v, and if the output signal exceeds the comparison level v, the comparator 43 generates an output onto the eye ball detection signal line 14.

In the above arrangement, the camera control circuit 11 generates operation clocks on the basis of the oscillator 12, and uses the generated clocks for its operation. In addition, the circuit 11 supplies the operation clocks to the area sensor IC 4. The operation clocks are supplied to the sensor driving circuit 17 for controlling the area sensor IC 4. The sensor driving circuit 17 operates based on the clocks, as shown in the timing charts of FIGS. 7 and 8.

As shown in FIG. 8, ON/OFF signals LED0 and LED1 for a plurality of illumination light sources sequentially and repetitively change to an "H" state (ON signals) to sequentially and repetitively turn on the infrared light-emitting diodes 5 and 6 as the illumination light sources.

FIG. 7 shows the driving timings and the like in a case wherein an eye is detected when one of the ON/OFF signals LED0 and LED1 for the illumination light sources changes to the "H" state (ON signal), and the infrared light-emitting diode 5 or 6 is turned on. A signal LED in FIG. 7 corresponds to one of the ON/OFF signals LED0 and LED1 for the illumination light sources shown in FIG. 8. FIG. 8 shows the driving timings and the like in a case wherein an eye is not detected and the detection is repeated. Note that the scale of the abscissa (time base) of FIG. 7 is enlarged to about twice that of FIG. 8, and FIG. 7 illustrates only the timings in a period t0 in FIG. 8 in the enlarged scale.

phase-1: All the emitter reset signal PVC and the sample & hold signals PSH0 and PSH1 are set at "H" to turn on the MOS transistors 32, 33, and 35, and the corresponding MOS transistors in the respective blocks, and to reset, to the ground potential, the emitter outputs of the transistor 31 and the corresponding NPN transistors of the sensor portions of the respective pixels, and the sample & hold capacitors 34 and 36 and the corresponding sample & hold capacitors in the respective blocks.

phase-2: The emitter reset signal PVC and the sample & hold signals PSH0 and PSH1 are reset to "L", and the base reset signal PBR is set at "L", so that the MOS transistor 29 and the corresponding MOS transistors of the respective pixels reset the bases of the NPN transistors (corresponding to the transistor 31) of the sensor portions of the respective pixels and the sensor capacitors (corresponding to the capacitor 30) connected thereto to the base reset potential VBR.

phase-3: After the bases are reset, the base reset signal PBR is reset to "H", and the sample & hold signal PSH0 is set at "H". More specifically, the MOS transistors (corresponding to the transistor 33) commonly connect the sample & hold capacitors (corresponding to the capacitor 34) of the respective blocks to the emitter outputs of all the pixels constituting each block, and thereafter, this state is maintained for a required accumulation time. In this state, the bases of the NPN transistors (corresponding to the transistor 31) of the sensor portions of the respective pixels and the sensor capacitors (corresponding to the capacitor 30) connected thereto accumulate charges generated by photoelectric conversion in correspondence with the amount of light incident on the photosensitive portions of the respective pixels, and their potentials increase in correspondence with the amount of light and the accumulation time. The emitter outputs of the NPN transistors (corresponding to the transistor 31) of the sensor portions of the respective pixels rise in correspondence with the increase in base potential while the base-emitter paths are biased. The emitters of the NPN transistors (corresponding to the transistor 31) of the sensor portions of the respective pixels in a single block are commonly connected to each other in accordance with the highest one of the base potentials of the NPN transistors (corresponding to the transistor 31) of the respective pixels in the block, thus determining the emitter output. More specifically, a signal of the brightest pixel in the block is obtained from the emitter output of the block as a signal of the block, and is supplied to the sample & hold capacitor (corresponding to the capacitor 34) of the block via the MOS transistor (corresponding to the transistor 33) of the block.

phase-4: After an elapse of the accumulation time, the sample & hold signal PSH0 is reset to "L" to turn off the MOS transistors (corresponding to the transistor 33). In this manner, signals, upon completion of the accumulation time, of the brightest pixels in the respective blocks during the accumulation time are held in the corresponding sample & hold capacitors (corresponding to the capacitor 34).

phase-5: The emitter reset signal PVC is set at "H" to set the MOS transistor 32 and the corresponding MOS transistors in the respective blocks in the ON state, and to reset the emitter outputs of the transistor 31 and the corresponding NPN transistors in the sensor portions of the respective pixels to the ground potential.

phase-6: The emitter reset signal PVC is reset to "H", and the base reset signal PBR is set at "L", so that the MOS transistor 29 and the corresponding MOS transistors in the respective pixels reset the bases of the NPN transistors (corresponding to the transistor 31) of the sensor portions of the respective pixels and the sensor capacitors (corresponding to the capacitor 30) connected thereto to the base reset potential VBR.

phase-7: After the bases are reset, the base reset signals PBR are reset to "H", and the sample & hold signal PSH1 is set at "H". More specifically, the MOS transistors (corresponding to the transistor 35) commonly connect the sample & hold capacitors (corresponding to the capacitor 36) of the respective blocks to the emitter outputs of all the pixels constituting each block. At the same time, the ON/OFF signal LED0 or LED1 for the illumination light sources is set at "H" to turn on the infrared light-emitting diode 5 or 6 as the illumination light source. Then, this state is maintained for substantially the same accumulation time as that in which the sample and hold signal PSH0 is set at "H", i.e., the MOS transistors (corresponding to the transistor 33) commonly connect the sample & hold capacitors (corresponding to the capacitor 34) of the respective blocks to the emitter outputs of all the pixels constituting each block.

phase-8: After an elapse of the accumulation time, the sample & hold signal PSH1 is reset to "L" to turn off the MOS transistors (corresponding to the transistor 35). In this manner, signals, upon completion of the accumulation time, of the brightest pixels in the respective blocks during the accumulation time in which the infrared light-emitting diode 5 or 6 as the illumination light source is turned on are held in the corresponding sample & hold capacitors (corresponding to the capacitor 36).

With the above-mentioned operations, the sample & hold capacitors corresponding to the capacitor 34 and the sample & hold capacitors corresponding to the capacitor 36 in all the blocks respectively hold the signals obtained when the illumination light source is OFF and when the illumination light source is ON.

phase-9: A shift register reset signal PRST is set at "L" to cancel the reset state of the shift register 26, and read clocks PRD are supplied to the shift register 26 to operate it. In synchronism with the read clocks PRD, readout line clear signals are output to repeat the readout operation and the readout line clear operation. In this manner, readout signals Pout xy in units of blocks are sequentially output from the shift register 26 to set the switch means corresponding to the transistors 37 and 38 in the corresponding block in the ON state, and to supply the signals respectively obtained in the ON and OFF states of the illumination light source to the output lines out0 and out1. The operator 41 outputs the difference between the signals obtained in the ON and OFF states of the illumination light source on the output lines out0 and out1 to the terminal OUT. Since the output OUT corresponds to the difference between the signals obtained in the ON and OFF states of the illumination light source, it corresponds to a signal of only light emitted by the illumination light source. The output OUT is supplied to the signal discrimination circuit 20.

Before the shift register 26 advances and the output from the next block is made, a readout line clear signal PHC turns on the MOS transistors 40 and 39 as the switch means to reset the output lines out0 and out1 to the ground potential.

Thereafter, in response to the readout clocks PRD, the shift register 26 generates the next readout signal Pout x(y+1), and supplies the signals from the next block onto the output lines out0 and out1. As a result, a signal, corresponding to a signal of only light emitted by the illumination light source, from the next block is output to the output OUT. As described above, by repetitively supplying clocks using the readout clocks PRD and the readout line clear signal PHC, signal outputs from the respective blocks are obtained.

The image of an eye has various features. As one of these features, a Purkinje image as a regularly reflected image of light emitted by the illumination light source and reflected by the cornea is known. The cornea is a convex mirror surface having a radius of about 8 mm, and a Purkinje image as a reflected image of a relatively small illumination light source such as an infrared light-emitting diode appears as a bright point with a small area and a high luminance on the screen. By detecting this bright point, the approach of the eye can be detected.

The signal discrimination circuit 20 detects if the signal outputs of the respective blocks, which are sequentially output to the output OUT, include an output exceeding a predetermined signal level v. If a signal output exceeding the level v is included, the circuit 20 determines the approach of the eye, and generates an output onto the eye ball detecting signal line 14. In this embodiment, the output from each block corresponds to the luminance of a point with the highest luminance of the pixels constituting the block, and by checking the signal outputs from all the blocks, it can be confirmed if the high-luminance points in all the pixels include a point with a luminance exceeding the predetermined level v. Since the signal of the output OUT is subjected to external light removal, i.e., consists of only signal light from the illumination light source, any bright point with a predetermined signal level or higher can be considered as a Purkinje image, and when such a signal is detected, the approach of the eye can be determined.

The approach of the eye is detected once in the above-mentioned operations of phase-1 to phase-9, and after the timer 18 measures a time t1, the detection is repeated at periods t0, as shown in FIG. 8.

More specifically, the infrared light-emitting diodes 5 and 6 as the plurality of illumination light sources are sequentially turned on to obtain images at the predetermined time intervals t0, and the approach of the eye is discriminated based on the obtained images.

If the time interval t0 is sufficiently shorter than that required for the eye approaching operation of a user, natural operability can be assured even when detection operations are performed intermittently. The time interval t0 can be selected to be about 0.01 to 1 sec if the present invention is applied to a camera.

On the other hand, since the device of this embodiment does not require processing of a large amount of data such as readout image processing of all the pixels of the light-receiving means, the actual operation time of the device can be shortened to about $10^{-6}$ sec to $10^{-3}$ sec. Thus, the actual operation time of the device can be shortened very much, and it is advantageous for reducing the consumption of power of the device.

Figure 9:
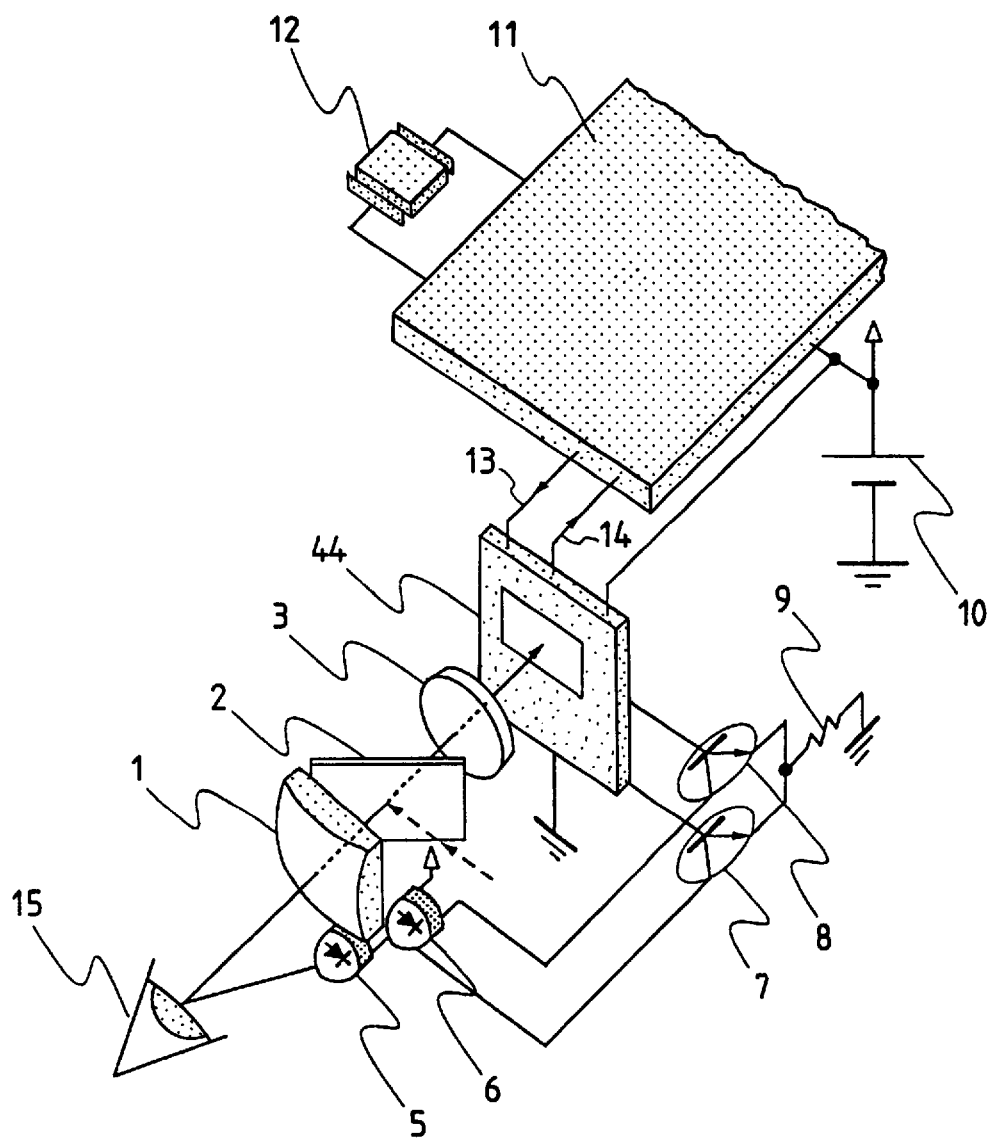
FIG. 9 is a schematic view of an eye ball detecting device for a camera according to the second embodiment of the present invention.

FIG. 9 shows an eye ball detecting device for a camera according to the second embodiment of the present invention.

Referring to FIG. 9, components 1 to 3 and 5 to 15 are the same as those in FIG. 1 in the first embodiment. An area sensor IC 44 corresponds to the IC 4 in FIG. 1 in the first embodiment, and has a light-receiving sensor unit for forming an image signal by photoelectrically converting an image.

Figure 10:
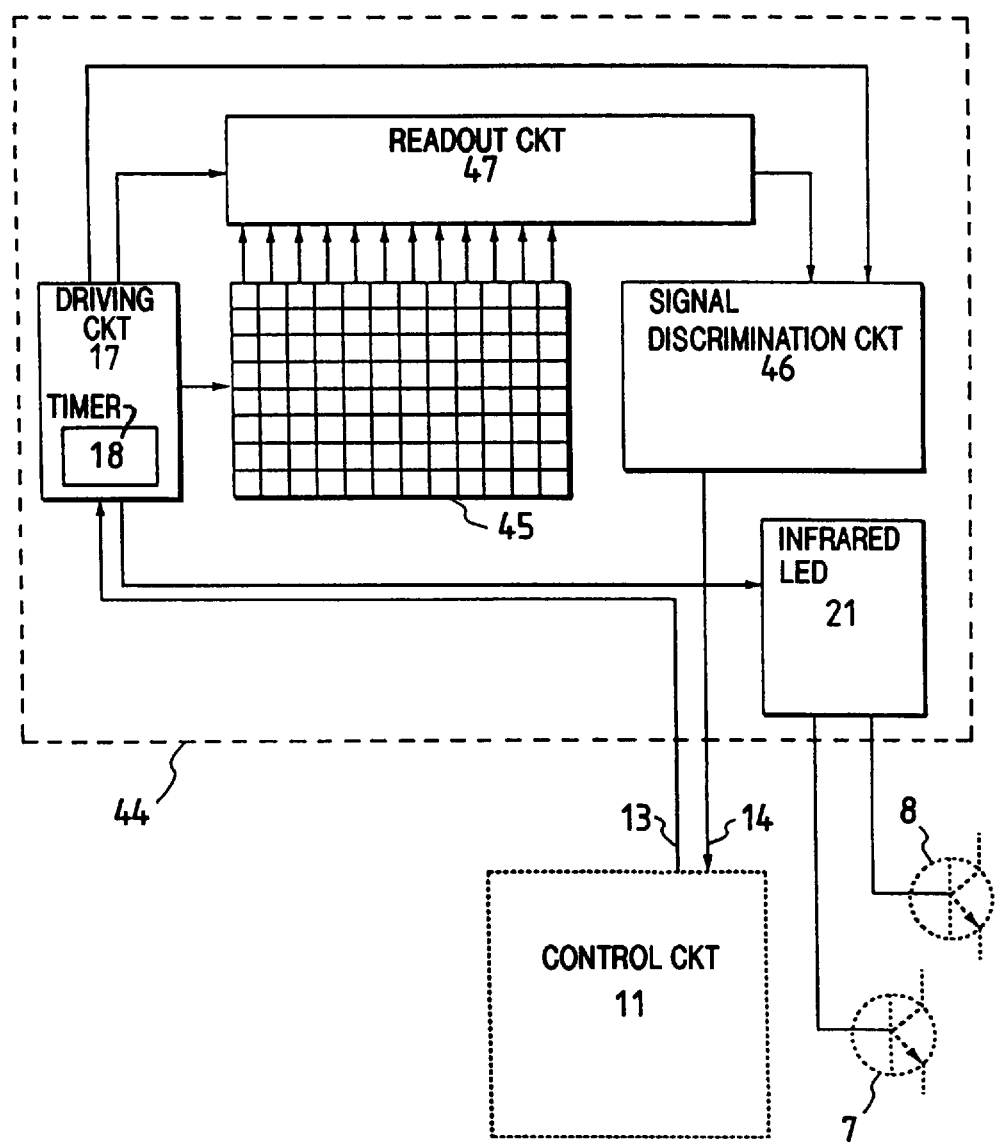
FIG. 10 is a block diagram of a sensor IC 44 shown in FIG. 9.

FIG. 10 shows the arrangement of the area sensor IC 44 of the eye ball detecting device for a camera shown in FIG. 9. The area sensor IC 44 is constituted by components 17, 18, 21, 45, 46, and 47, and is connected to the components 7, 8, 11, 13, and 14 shown in FIG. 9.

Referring to FIG. 10, an area sensor unit 45 in the area sensor IC 44 serves as a light-receiving sensor constituted by a large number of pixels, and each pixel constituting the unit 45 has a size as large as a bright point as a Purkinje image. Components 17, 18, and 21 are the same as those in FIG. 2. A readout circuit 47 sequentially reads out image signals from the area sensor unit 45 in response to timing signals from the sensor driving circuit 17, and supplies the readout signals to a signal discrimination circuit 46. The signal discrimination circuit 46 discriminates, based on the image signals from the readout circuit 47, if the eye approaches the finder.

Figure 11:
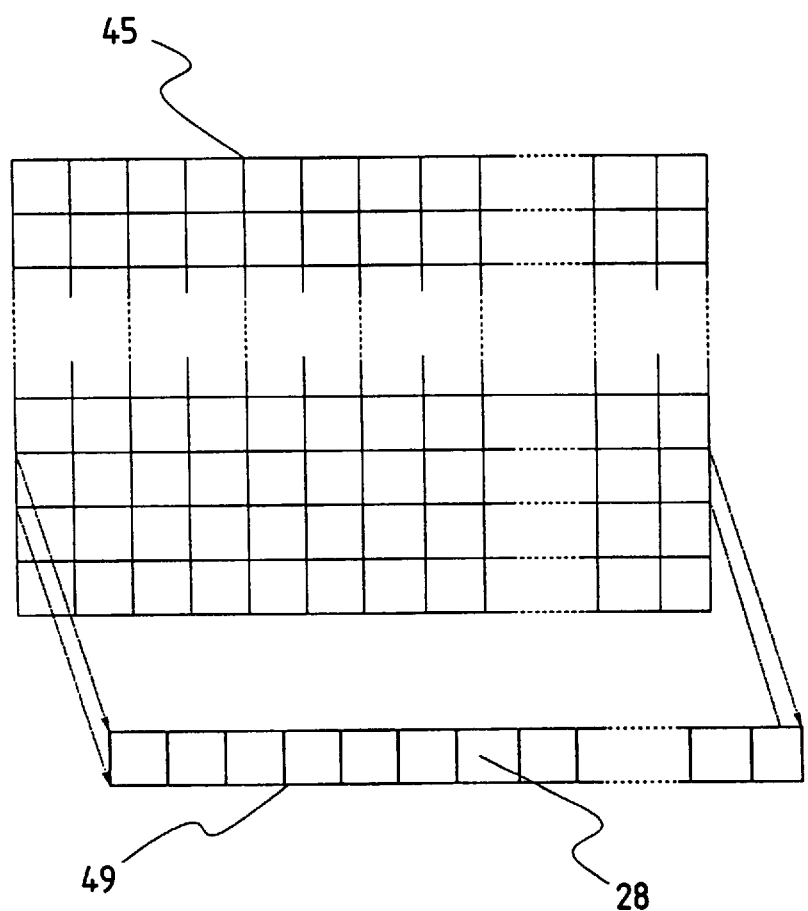
FIG. 11 is a view showing the relationship between the pixels and blocks of an area sensor unit 45 shown in FIG. 10.

FIG. 11 shows divided blocks obtained by dividing the screen surface of the area sensor unit 45. Each block has a long-side direction agreeing with the horizontal direction and a short-side direction agreeing with the vertical direction, and is defined by pixels from one end to the other end of the screen in the horizontal direction and by one pixel in the vertical direction, i.e., one row in the horizontal direction.

Figure 12:
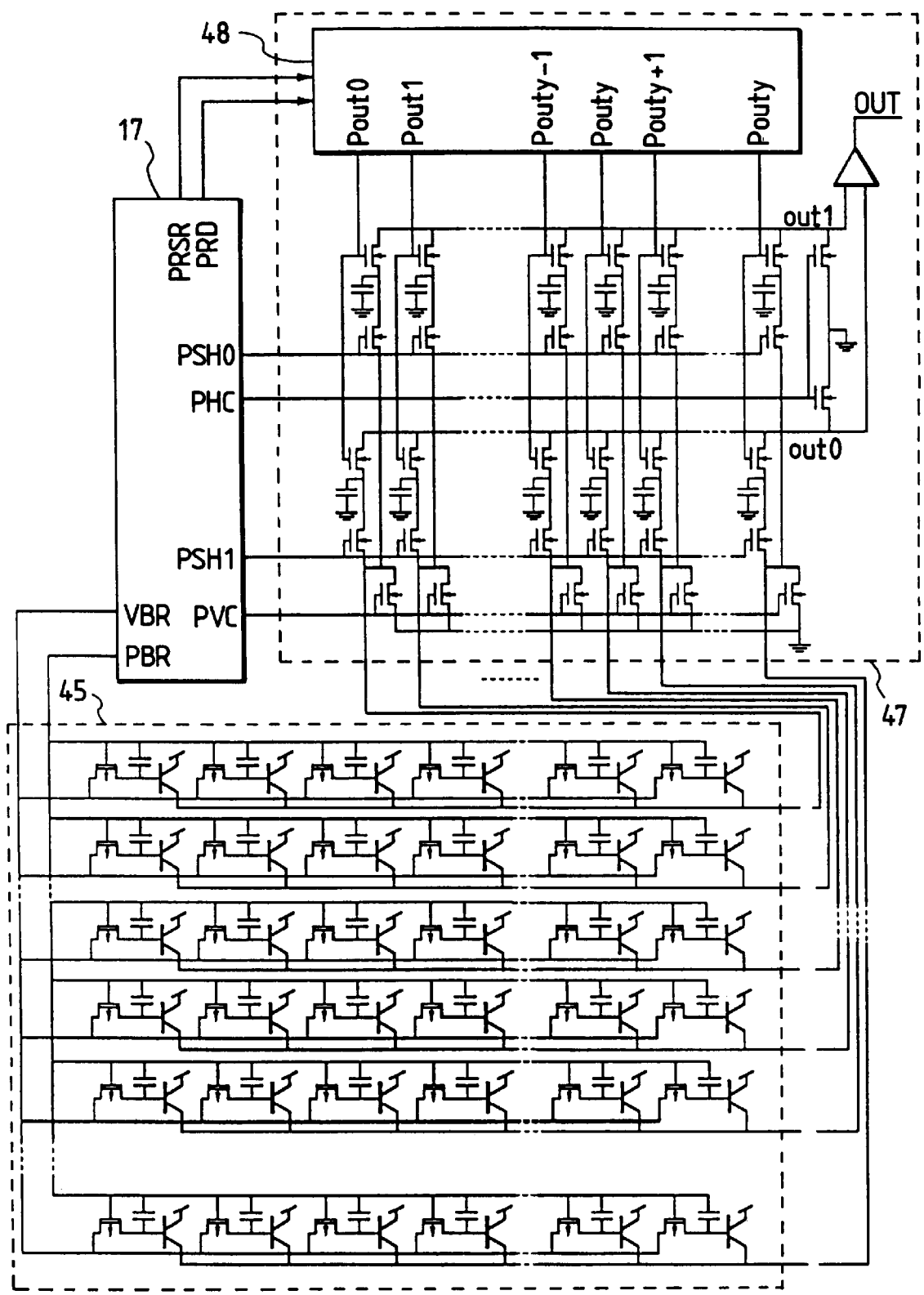
FIG. 12 is a circuit diagram showing the arrangement of the area sensor unit 45 and a readout circuit 47 shown in FIG. 10 when an area sensor is constituted by a nondestructive readout photoelectric conversion element.

FIG. 12 shows the arrangement of the area sensor unit and the readout circuit when the area sensor is constituted by a nondestructive readout photoelectric conversion element. Referring to FIG. 12, a nondestructive readout photoelectric conversion element driving circuit 17 corresponds to the sensor driving circuit 17 in FIG. 10. A nondestructive readout photoelectric conversion element sensor unit 45 corresponds to the area sensor unit 45 in FIG. 10. A readout circuit 47 corresponds to the circuit 47 in FIG. 10. The readout circuit 47 includes a shift register 48 for sequentially supplying the readout timings of the respective blocks.

Figure 13:
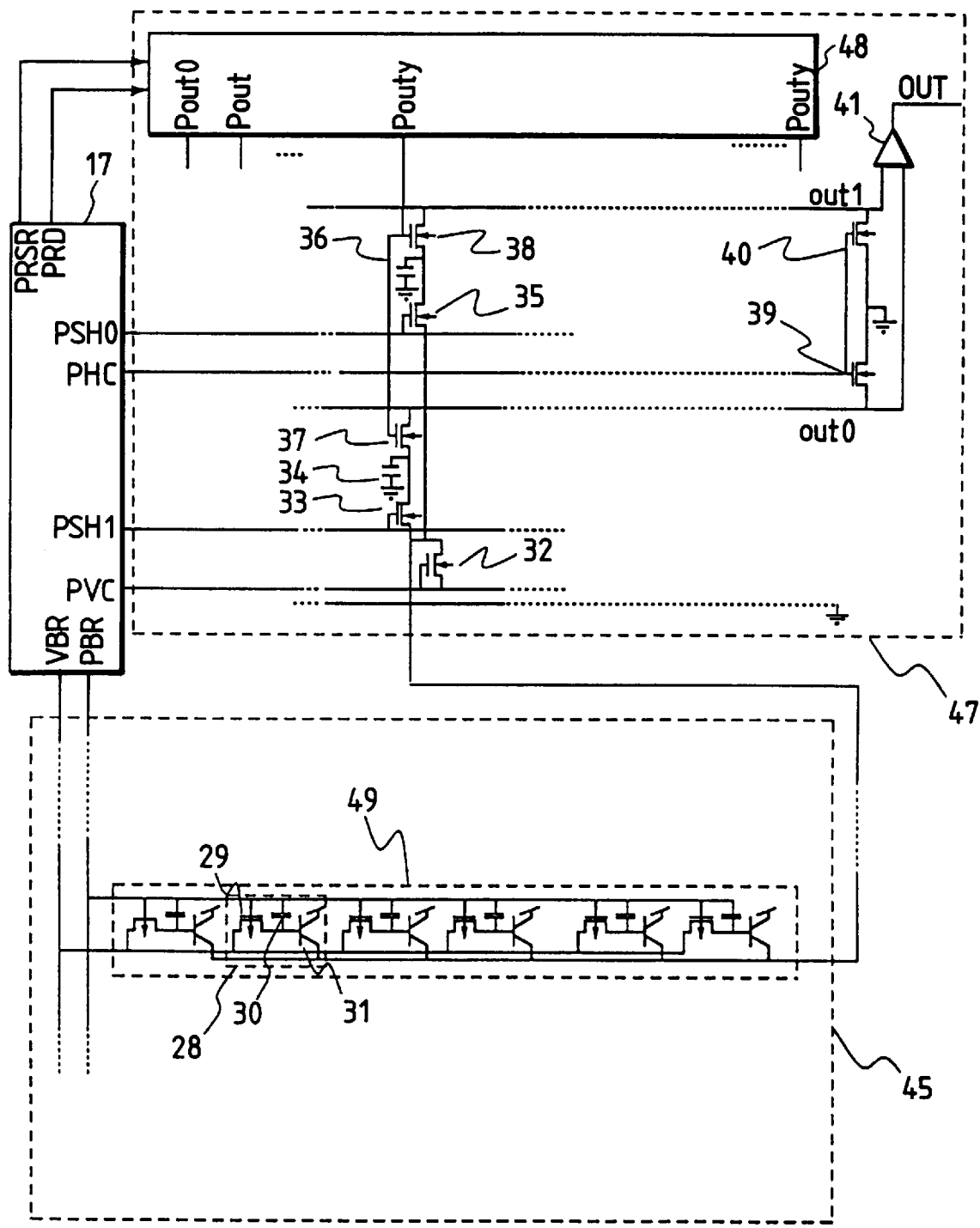
FIG. 13 is a partial circuit diagram showing the arrangement for one block to explain the sensor arrangement shown in FIG. 12 and its operation for the sake of convenience.

FIG. 13 is a partial circuit diagram showing the arrangement for one block to explain the sensor arrangement shown in FIG. 12 and its operation for the sake of convenience. Referring to FIG. 13, components 17, 45, 47, and 48 are the same as those in FIG. 12. One block 49 is constituted by a plurality of pixels. In addition, components 28 to 41 are the same as those in FIG. 5 in the first embodiment.

More specifically, a cell 28 constitutes one pixel of the image sensor. The cell 28 includes a MOS transistor 29 which serves as switch means for resetting the base potential of a transistor 31 in accordance with a base reset signal PBR supplied from the driving circuit 17, a sensor capacitor 30, and the NPN transistor 31. The transistor 31 serves as a sensor portion of the nondestructive readout photoelectric conversion element. More specifically, the base or a portion connected to the base of the transistor 31 serves as a photosensitive portion and a signal accumulation portion, and the transistor 31 outputs, from its emitter, a voltage according to a base potential corresponding to the charge amount accumulated on its base. The outputs (emitter outputs) from the pixels constituting each block are commonly supplied to the readout circuit 47 as an output from the block. The readout circuit 47 includes a MOS transistor 32 serving as switch means for resetting the block output to the ground potential in accordance with an emitter reset signal PVC supplied from the driving circuit, a MOS transistor 33 serving as switch means for supplying the block output to a sample & hold capacitor 34 in accordance with a sample & hold signal PSH1 supplied from the driving circuit 17, the sample & hold capacitor 34 for sampling and holding the block output, a MOS transistor 35 serving as switch means for supplying the block output to a sample & hold capacitor 36 in accordance with a sample & hold signal PSH0 supplied from the driving circuit 17, the sample & hold capacitor 36 for sampling and holding the block output, a MOS transistor 37 serving as switch means for outputting a signal, which is sampled and held by the capacitor 34 in accordance with the sample & hold signal PSH0, onto an output line out0 in accordance with an output signal Pout y for each block supplied from the shift register 48, a MOS transistor 38 serving as switch means for outputting a signal, which is sampled and held by the capacitor 36 in accordance with the sample & hold signal PSH1, onto an output line out1 in accordance with an output signal Pout y for each block supplied from the shift register, MOS transistors 39 and 40 serving as switch means for respectively resetting the output lines out0 and out1 to the ground potential in accordance with a reset signal PHC supplied from the driving circuit 17, and an operator 41 for outputting the difference between the signals on the output lines out0 and out1 to a terminal OUT.

Components 32 to 38 or equivalents are arranged in correspondence with block outputs, and constitute the same circuits as those constituted by the components 32 to 38. These components are also connected to the driving circuit 17, the shift register 48, and the output lines out0 and out1, and constitute the readout circuit 47 together with the shift registers 48, the MOS transistors 39 and 40, and the operator 41.

Figure 14:
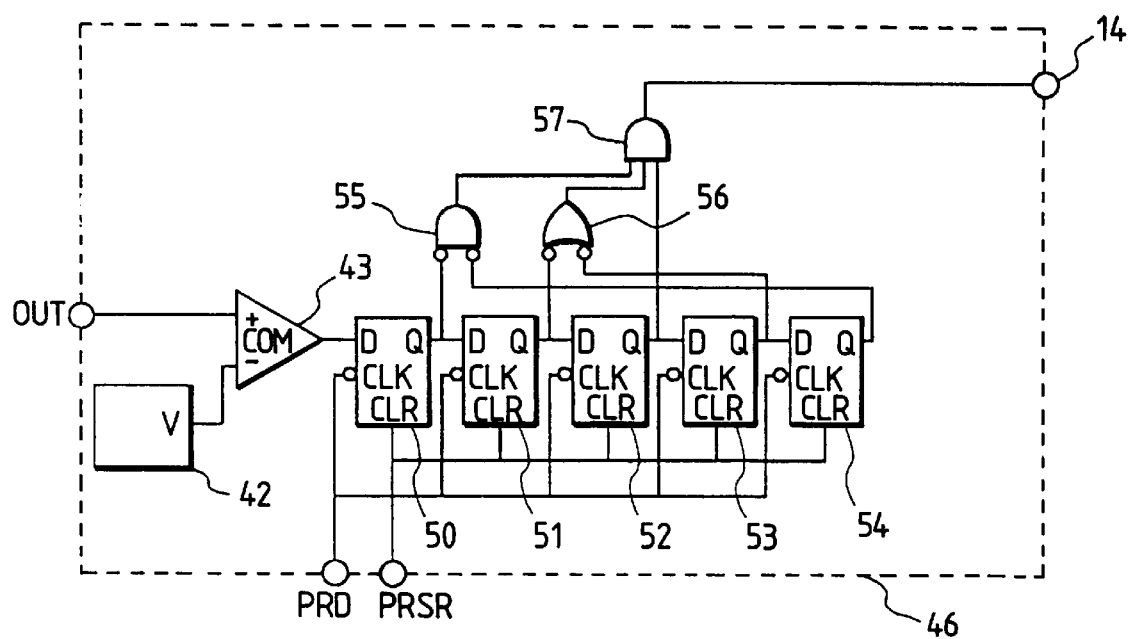
FIG. 14 is a circuit diagram showing the arrangement of a signal discrimination circuit 46 shown in FIG. 10.

FIG. 14 shows the arrangement of the signal discrimination circuit 46 shown in FIG. 10. Referring to FIG. 14, components 42 and 43 are the same as those in FIG. 6 in the first embodiment. That is, a constant voltage circuit 42 generates a predetermined comparison level v. A comparator 43 compares the output signal from the readout circuit 47, i.e., the output OUT from the operator 41 with the comparison level v, and if the output signal exceeds the comparison level v, the comparator 43 sets its output at "H". D flip-flops 50 to 54 constitute a shift register which receives the output from the comparator 43. A negative input AND gate 55 receives the outputs from the first D flip-flop 50 and the fifth D flip-flop 54 of the shift register (50 to 54), and supplies its output to an AND gate 57. A negative input OR gate 56 receives the outputs from the second D flip-flop 51 and the fourth D flip-flop 53 of the shift register (50 to 54), and supplies its output to the AND gate 57. The AND gate 57 receives the outputs from the negative input AND gate 55, the negative input OR gate 56, and the third D flip-flop 52 of the shift register (50 to 54), and its output is connected to the eye ball detecting signal line 14.

In the above-mentioned arrangement, the area sensor IC 44, the area sensor unit 45, the readout circuit 47, the shift register 48, and the block 49 respectively correspond to the area sensor IC 4, the area sensor unit 16, the readout circuit 19, the shift register 26, and the block 27 in the first embodiment. As in the first embodiment, the camera control circuit 11 generates operation clocks on the basis of the output from the oscillator 12, and these clocks are supplied to the area sensor IC 44. In response to these clocks, the area sensor IC 44 operates, as shown in the timing charts of FIGS. 7 and 8. With this operation, the signal outputs from the respective blocks are sequentially obtained from the output OUT as in the first embodiment.

The signal discrimination circuit 46 discriminates the approach of the eye on the basis of the signal outputs from the respective blocks, which are sequentially output to the output OUT, and supplies the discrimination result onto the eye ball detecting signal line 14. In the arrangement of the signal discrimination circuit 46 shown in FIG. 14, each of the signal outputs from the respective blocks, which are sequentially output to the output OUT, is compared by the comparator 43 with the predetermined comparison level v generated by the constant voltage circuit 42, which level corresponds to the luminance discrimination level of a Purkinje image. The comparison result is supplied to the shift register (50 to 54). The shift register (50 to 54) sequentially fetches and transfers the comparison results of the respective blocks in synchronism with readout signals generated by the driving circuit 17. Therefore, the outputs from the respective stages of the shift register (50 to 54) correspond to an array of the comparison results from five vertically continuous blocks (rows) on the sensor. For example, if the output from the third D flip-flop 52 of the shift register (50 to 54) corresponds to a comparison result D(y) of a y-th block (row), the first D flip-flop 50 of the shift register (50 to 54) outputs a comparison result D(y+2) of a (y+2)-th block (row); the second D flip-flop 51 of the shift register (50 to 54) outputs a comparison result D(y+1) of a (y+1)-th block (row); the fourth D flip-flop 53 of the shift register (50 to 54) outputs a comparison result D(y−1) of a (y−1)-th block (row); and the fifth D flip-flop 54 of the shift register (50 to 54) outputs a comparison result D(y−2) of a (y−2)-th block (row). Via the gates 55, 56, and 57, the following output is obtained:

$$D(y) \cdot (\overline{D(y-1)} + \overline{D(y+1)}) \cdot \overline{D(y-2)} \cdot \overline{D(y+2)}$$

More specifically, when only the y-th block or only two blocks, i.e., the y-th block and its neighboring block include pixels with a high luminance, the signal discrimination circuit 46 supplies an output onto the eye ball detecting signal line 14. In this embodiment, the output from each block corresponds to the luminance of a point with the highest luminance of pixels constituting the block, and it can be confirmed by checking the signal outputs from all the blocks if the high-luminance points of all the pixels include a point exceeding the predetermined level v. In addition, only a bright point which has a size equal to or smaller than a predetermined value (twice the width, in the short-side direction, of the block) in the vertical direction on the screen is detected. Since the signal of the output OUT is subjected to external light removal, i.e., consists of only signal light from the illumination light source, any bright point with a predetermined signal level or higher and a predetermined size or less can be considered as a Purkinje image, and when such a signal is detected, the approach of the eye can be determined. The reason why the upper limit of the size of the bright point is set to be two pixels (two blocks (rows)) although the size of the Purkinje image is assumed to be that of one pixel is that the bright point may often be located between two adjacent pixels, as a matter of course.

Figure 15:
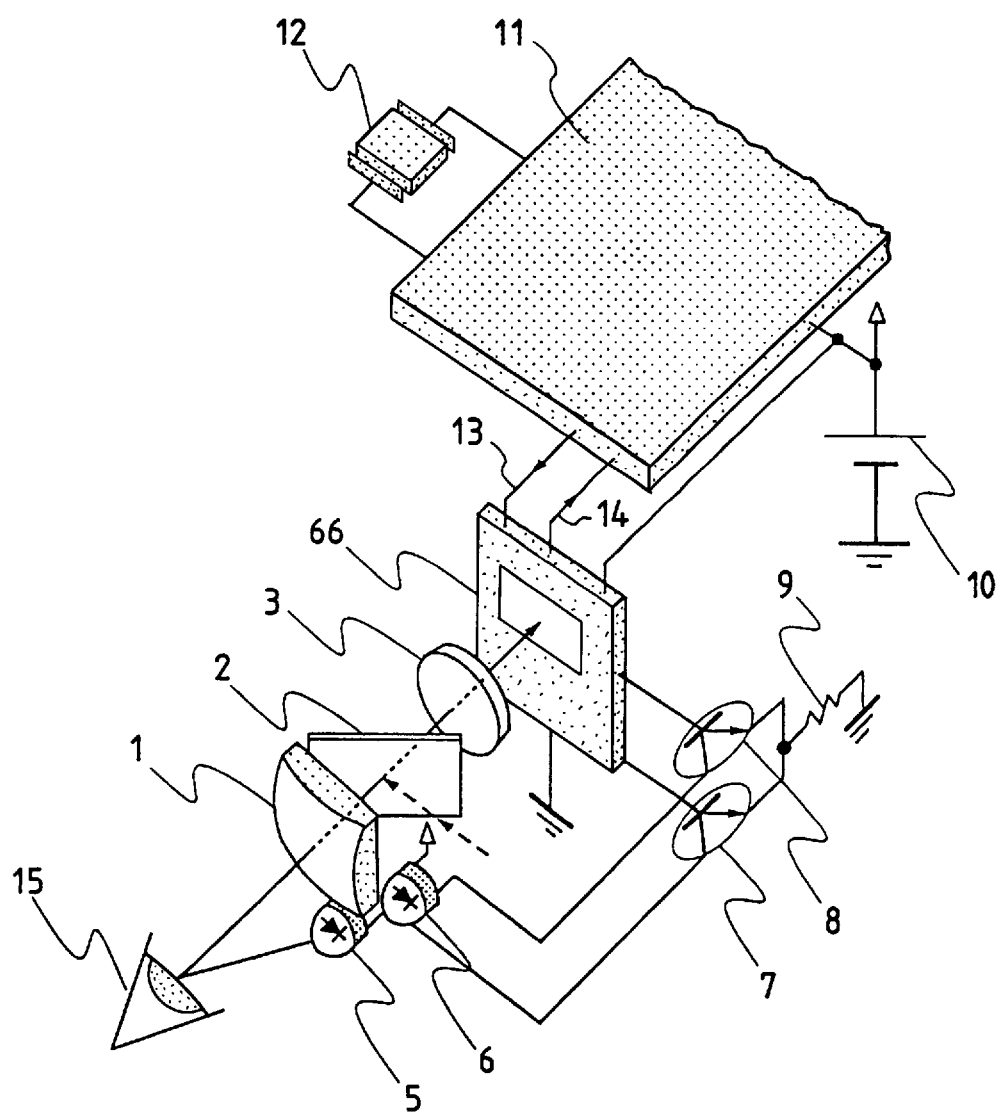
FIG. 15 is a schematic view of an eye ball detecting device for a camera according to the second embodiment of the present invention.

FIG. 15 shows an eye ball detecting device for a camera according to the third embodiment of the present invention. Referring to FIG. 15, components 1 to 3 and 5 to 15 are the same as those in FIG. 1 in the first embodiment or in FIG. 9 in the second embodiment. An area sensor IC 66 corresponds to the IC 4 in FIG. 1 in the first embodiment or the IC 44 in FIG. 9 in the second embodiment, and has a light-receiving sensor unit for forming an image signal by photoelectrically converting an image.

Figure 16:
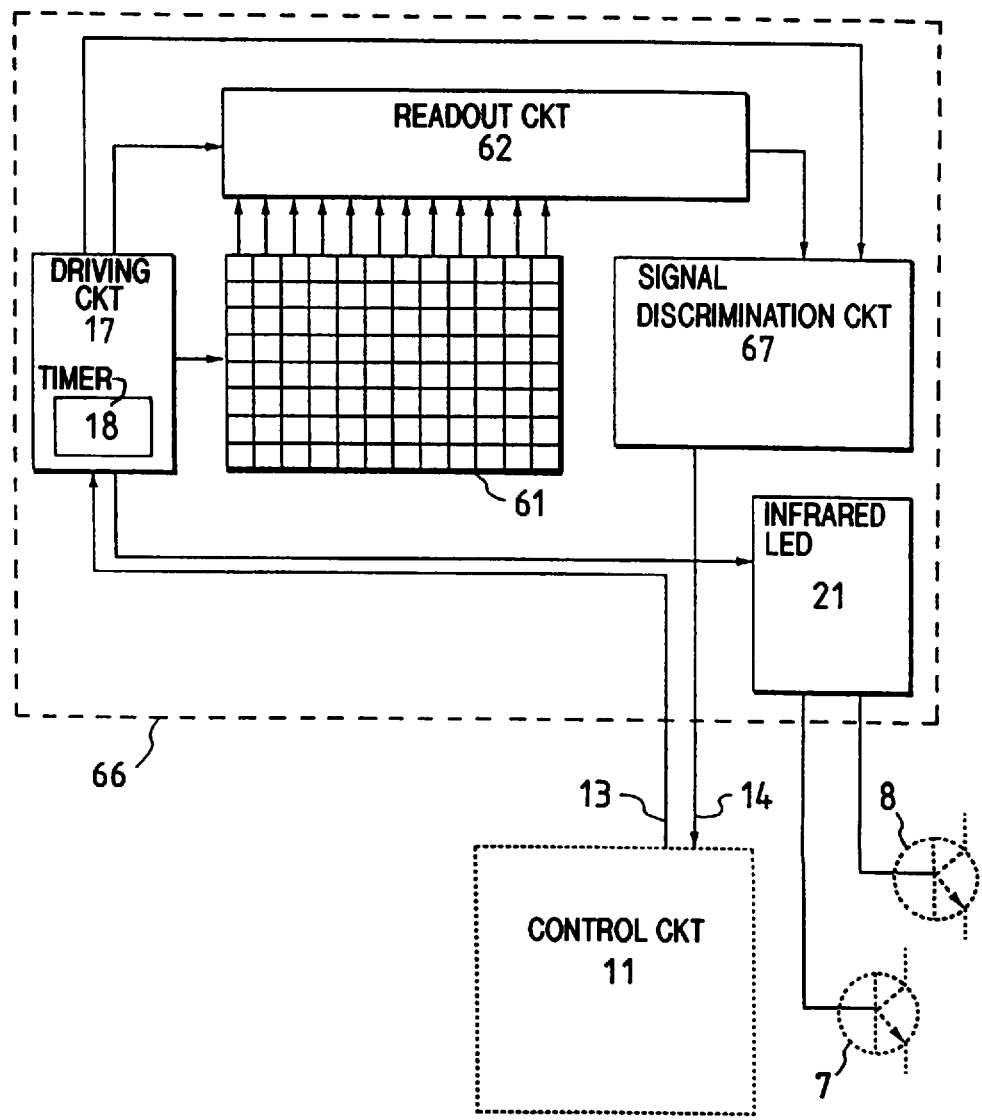
FIG. 16 is a block diagram of a sensor IC 66 shown in FIG. 15.

FIG. 16 shows the arrangement of the area sensor IC 66 of the eye ball detecting device for a camera shown in FIG. 15. The area sensor IC 66 is constituted by components 17, 18, 21, 61, 62, and 67, and is connected to the components 7, 8, 11, 13, and 14 shown in FIG. 15.

Referring to FIG. 16, an area sensor unit 61 in the area sensor IC 66 serves as a light-receiving sensor constituted by a large number of pixels, and each pixel constituting the unit 61 has a size as large as a bright point as a Purkinje image. Components 17, 18, and 21 are the same as those in FIG. 2 in the first embodiment or FIG. 9 in the second embodiment. A readout circuit 62 sequentially reads out image signals from the area sensor unit 61 in response to timing signals from the sensor driving circuit 17, and supplies the readout signals to a signal discrimination circuit 67. The signal discrimination circuit 67 discriminates, based on the image signals from the readout circuit 62, if the eye approaches the finder.

Figure 17:
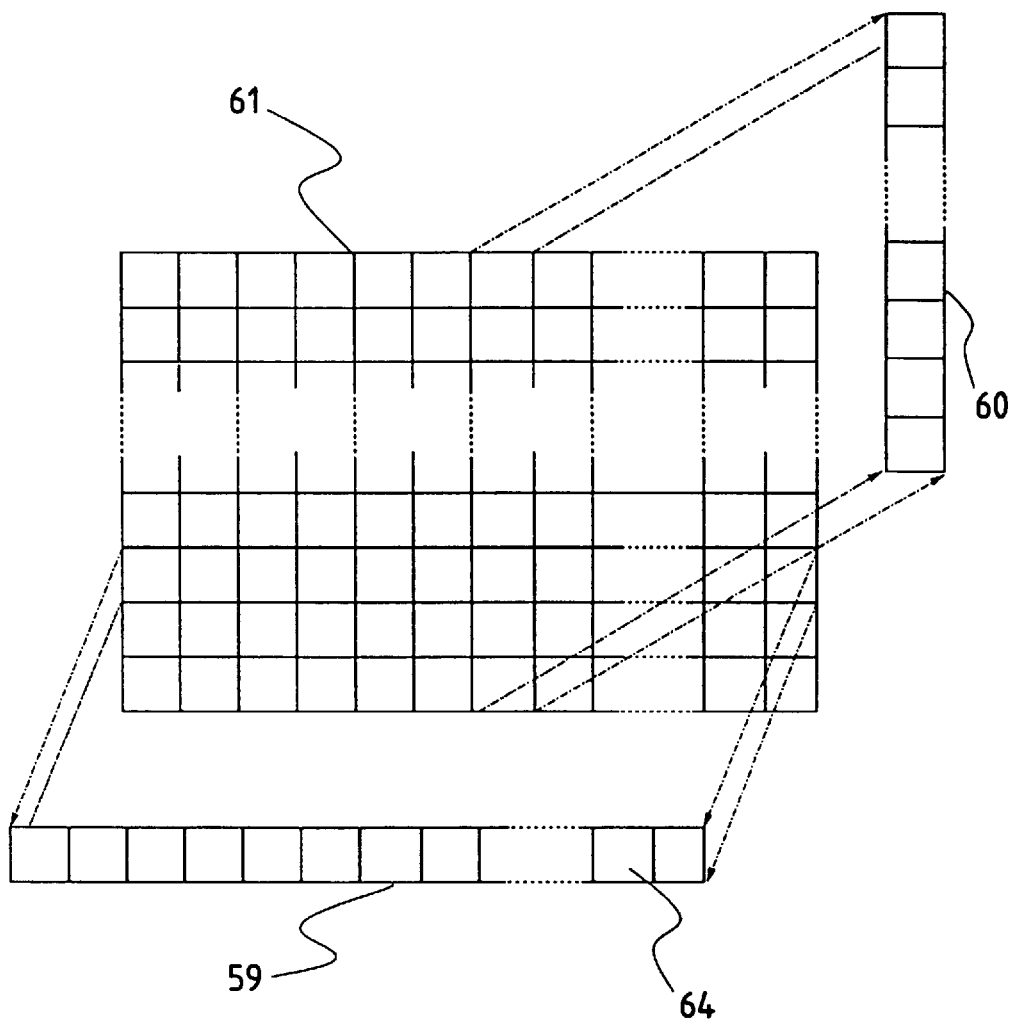
FIG. 17 is a view showing the relationship between the pixels and blocks of an area sensor unit 61 shown in FIG. 16.

FIG. 17 shows divided blocks obtained by dividing the screen surface of the area sensor unit 61. Each block of a first block group has a long-side direction agreeing with the horizontal direction and a short-side direction agreeing with the vertical direction, and is defined by pixels from one end to the other end of the screen in the horizontal direction and by one pixel in the vertical direction, i.e., one row in the horizontal direction. On the other hand, each block of a second block group has a long-side direction agreeing with the vertical direction and a short-side direction agreeing with the horizontal direction, and is defined by pixels from one end to the other end of the screen in the vertical direction and by one pixel in the horizontal direction, i.e., one column in the vertical direction. Therefore, each pixel belongs to two blocks, i.e., one block belonging to the first block group and one block belonging to the second block group.

Figure 18:
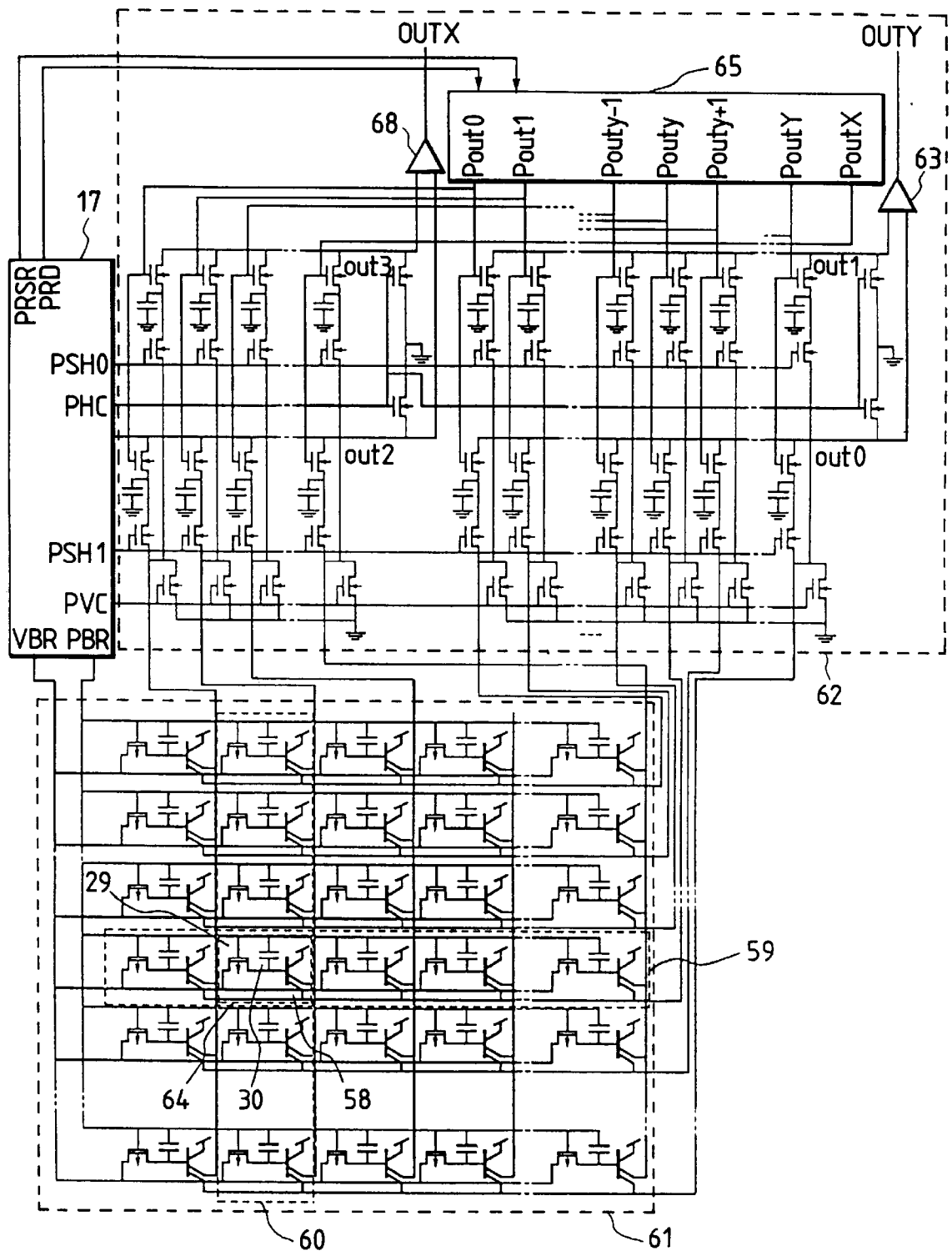
FIG. 18 is a circuit diagram showing the arrangement of the area sensor unit 61 and a readout circuit 62 shown in FIG. 16 when an area sensor is constituted by a nondestructive readout photoelectric conversion element.

FIG. 18 shows the arrangement of the area sensor unit and the readout circuit when the area sensor is constituted by a nondestructive readout photoelectric conversion element. Referring to FIG. 18, a nondestructive readout photoelectric conversion element driving circuit 17 corresponds to the sensor driving circuit 17 in FIG. 16. A nondestructive readout photoelectric conversion element sensor unit 61 corresponds to the area sensor unit 61 in FIGS. 16 and 17. A readout circuit 62 corresponds to the circuit 62 in FIG. 16. The readout circuit 62 includes a shift register 48 for sequentially supplying readout timings to the respective blocks belonging to the first block group and the respective blocks belonging to the second block group.

A cell 64 constitutes one pixel of the image sensor. The cell 64 includes a MOS transistor 29 which is similar to the transistor 29 in FIG. 5 in the first embodiment or in FIG. 13 in the second embodiment, and serves as switch means for resetting the base potential of a transistor 58 in accordance with a base reset signal PBR supplied from the driving circuit 17, a sensor capacitor 30 which is similar to the capacitor 30 in FIG. 5 in the first embodiment or in FIG. 13 in the second embodiment, and the NPN transistor 58. The transistor 58 has two emitters, and serves as a sensor portion of the nondestructive readout photoelectric conversion element. More specifically, the base (or a portion connected to the base) of the transistor 58 serves as a photosensitive portion and a signal accumulation portion, and the transistor 58 outputs, from its two emitters, a voltage according to a base potential corresponding to the charge amount accumulated on its base. The outputs (emitter outputs) from the pixels constituting each block are commonly supplied to the readout circuit 62 as an output from the block. One pixel (e.g., the pixel 64) belongs to two blocks, i.e., a block (a block 59) belonging to the first block group and a block (a block 60) belonging to the second block group (for example, the pixel 64 belongs to two blocks, i.e., the block 59 belonging to the first block group and the block 60 belonging to the second block group). In this case, when the two emitters of each transistor corresponding to the transistor 58 in each pixel are connected in units of blocks, the two blocks are independently connected to a common pixel. Circuits in units of blocks in the readout circuit 62 are the same as those in the readout circuit 47 in the second embodiment, and a detailed description thereof will be omitted. Note that the outputs are made in units of block groups. An operator 63 outputs the difference between signals on output lines out0 and out1 to an output OUTY of the first block group, and an operator 68 outputs the difference between signals on output lines out2 and out3 to an output OUTX of the second block group.

Figure 19:
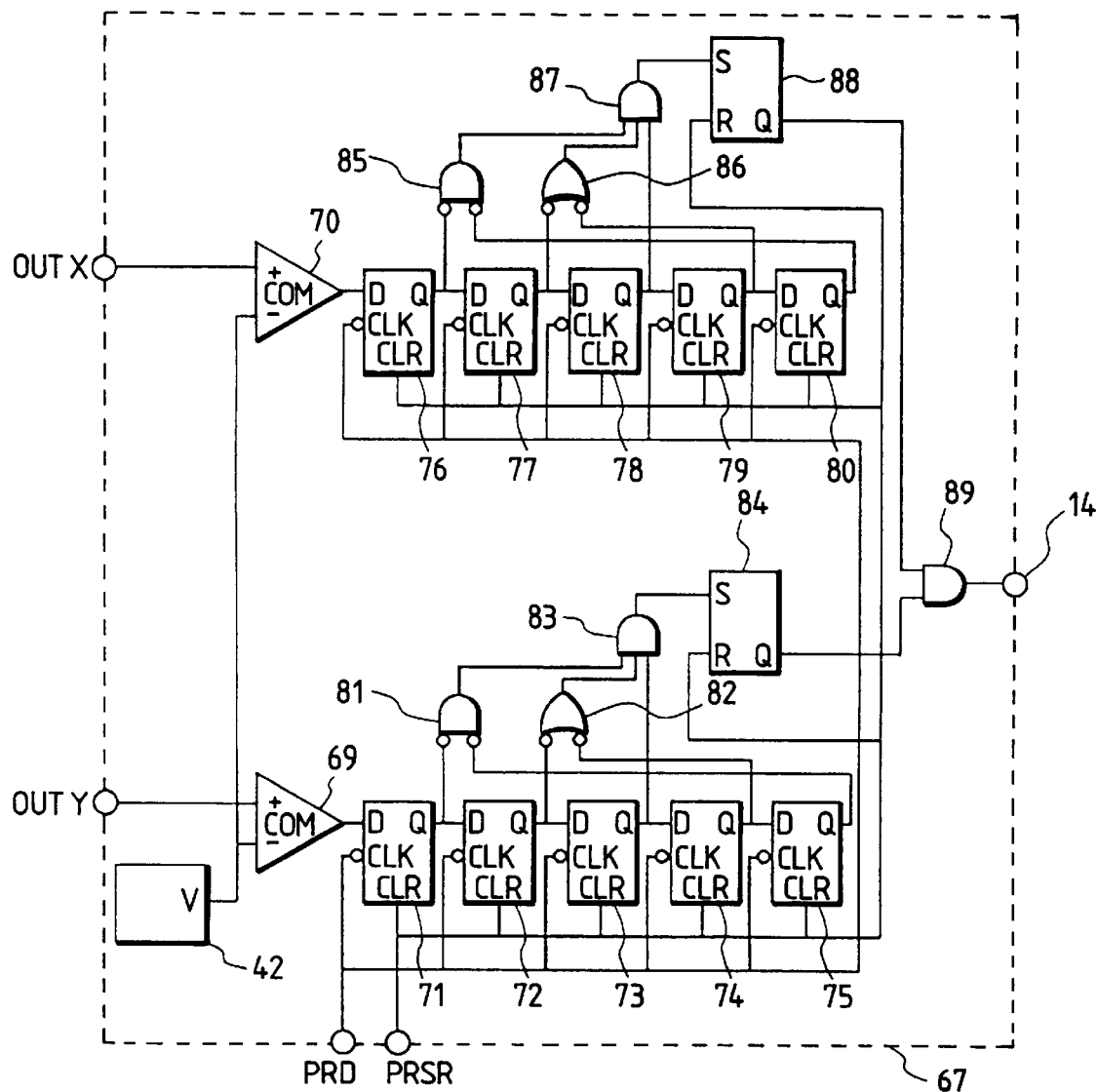
FIG. 19 is a circuit diagram showing the arrangement of a signal discrimination circuit 67 shown in FIG. 16.

FIG. 19 shows the arrangement of the signal discrimination circuit 67 shown in FIG. 16. Referring to FIG. 19, a constant voltage circuit 42 is similar to that in FIG. 6 in the first embodiment or in FIG. 14 in the second embodiment, and generates a predetermined comparison level v. Comparators 69 and 70 respectively compare the output signals from the readout circuit 62, i.e., the output OUTY from the operator 63 and the output OUTX from the operator 68 with the comparison level v, and set their outputs at "H" when the outputs exceed the comparison level v. D flip-flops 71 to 75 constitute a shift register which receives the output from the comparator 69. D flip-flops 76 to 80 constitute a shift register which receives the output from the comparator 70. A negative input AND gate 81 receives the outputs from the first D flip-flop 71 and the fifth D flip-flop 75 of the shift register (71 to 75), and supplies its output to an AND gate 83. A negative input OR gate 82 receives the outputs from the second D flip-flop 72 and the fourth D flip-flop 74 of the shift register (71 to 75), and supplies its output to the AND gate 83. The AND gate 83 receives the outputs from the negative input AND gate 81, the negative input OR gate 82, and the third D flip-flop 73 of the shift register (71 to 75), and its output is connected to the set input of an R-S flip-flop 84. A negative input AND gate 85 receives the outputs from the first D flip-flop 76 and the fifth D flip-flop 80 of the shift register (76 to 80), and supplies its output to an AND gate 87. A negative input OR gate 86 receives the outputs from the second D flip-flop 77 and the fourth D flip-flop 79 of the shift register (76 to 80), and supplies its output to the AND gate 87. The AND gate 87 receives the outputs from the negative input AND gate 85, the negative input OR gate 86, and the third D flip-flop 78 of the shift register (76 to 80), and its output is connected to the set input of an R-S flip-flop 88. The outputs from the two R-S flip-flops 84 and 88 are supplied to an AND gate 89, and the output from the AND gate 89 is connected to an eye ball detecting signal line 14.

In the above-mentioned arrangement, the area sensor IC 66, the area sensor unit 61, the readout circuit 62, and a shift register 65 respectively correspond to the area sensor IC 4, the area sensor unit 16, the readout circuit 19, and the shift register 26 in the first embodiment. As in the first embodiment, a camera control circuit 11 generates operation clocks on the basis of the output from an oscillator 12, and these clocks are supplied to the area sensor IC 66. In response to these clocks, the area sensor IC 66 operates, as shown in the timing charts of FIGS. 7 and 8. With this operation, the signal outputs from the respective blocks are sequentially obtained as in the first embodiment. In this case, the signal outputs from the respective blocks of the first and second block groups are parallelly output from the outputs OUTY and OUTX.

The signal discrimination circuit 67 discriminates the approach of the eye on the basis of the signal outputs from the respective blocks, which are sequentially output to the outputs OUTX and OUTY, and supplies the discrimination result onto the eye ball detecting signal line 14. In the arrangement of the signal discrimination circuit 67 shown in FIG. 19, each of the signal outputs from the respective blocks, which are sequentially output to the output OUTY, is compared by the comparator 69 with the predetermined comparison level v generated by the constant voltage circuit 42, which level corresponds to the luminance discrimination level of a Purkinje image, and each of the signal outputs from the respective blocks, which are sequentially output to the output OUTX, is compared by the comparator 70 with the predetermined comparison level v. These comparison results are respectively supplied to the shift register (50 to 54) and the shift register (76 to 80).

The shift register (71 to 75) sequentially fetches and transfers the comparison results of the respective blocks belonging to the first block group in synchronism with readout signals generated by the driving circuit 17. Therefore, the outputs from the respective stages of the shift register (71 to 75) correspond to an array of the comparison results from five vertically continuous blocks (rows) on the sensor. For example, if the output from the third D flip-flop 73 of the shift register (71 to 75) corresponds to a comparison result Dy(n) of an n-th block (row), the first D flip-flop 71 of the shift register (71 to 75) outputs a comparison result Dy(n+2) of an (n+2)-th block (row); the second D flip-flop 72 of the shift register (71 to 75) outputs a comparison result Dy(n+1) of an (n+1)-th block (row); the fourth D flip-flop 74 of the shift register (71 to 75) outputs a comparison result Dy(n−1) of an (n−1)-th block (row); and the fifth D flip-flop 75 of the shift register (71 to 75) outputs a comparison result Dy(n−2) of an (n−2)-th block (row). Via the gates 81, 82, and 83, the following output is obtained:

$$Dy(n) \cdot \overline{(\overline{Dy(n-1)} + \overline{Dy(n+1)})} \cdot \overline{Dy(n-2)} \cdot \overline{Dy(n+2)}$$

More specifically, when only the n-th block or only two blocks, i.e., the n-th block and its neighboring block include pixels with a high luminance, the signal discrimination circuit 67 supplies a set signal to the R-S flip-flop 84.

Similarly, the shift register (76 to 80) sequentially fetches and transfers the comparison results of the respective blocks belonging to the second block group in synchronism with readout signals generated by the driving circuit 17. Therefore, the outputs from the respective stages of the shift register (76 to 80) correspond to an array of the comparison results from five horizontally continuous blocks (columns) on the sensor. For example, if the output from the third D flip-flop 78 of the shift register (76 to 80) corresponds to a comparison result Dx(n) of an n-th block (column), the first D flip-flop 76 of the shift register (76 to 80) outputs a comparison result Dx(n+2) of an (n+2)-th block (column); the second D flip-flop 77 of the shift register (76 to 77) outputs a comparison result Dx(n+1) of an (n+1)-th block (column); the fourth D flip-flop 79 of the shift register (76 to 80) outputs a comparison result Dx(n−1) of an (n−1)-th block (column); and the fifth D flip-flop 80 of the shift register (76 to 80) outputs a comparison result Dx(n−2) of an (n−2)-th block (column). Via the gates 85, 86, and 87, the following output is obtained:

$$Dx(n) \cdot \overline{(\overline{Dx(n-1)} + \overline{Dx(n-1)})} \cdot \overline{Dx(n-2)} \cdot \overline{Dx(n+2)}$$

More specifically, when only the n-th block or only two blocks, i.e., the n-th block and its neighboring block include pixels with a high luminance, the signal discrimination circuit 67 supplies a set signal to the R-S flip-flop 88.

With the above-mentioned operations, when a bright point which has a size equal to or smaller than two blocks in the vertical direction and a size equal to or smaller than two blocks in the horizontal direction is present on the screen, both the R-S flip-flops are set, and the AND gate 89, which calculates the AND of the outputs from these flip-flops, supplies an "H" output, i.e., an eye ball detecting signal, onto the eye ball detecting signal line 14 connected thereto.

In this embodiment, the output from each block corresponds to the luminance of a point with the highest luminance of pixels constituting the block, and it can be confirmed by checking the signal outputs from all the blocks if the high-luminance points of all the pixels include a point exceeding the predetermined level v. In addition, only a bright point which has a size equal to or smaller than a predetermined value (twice the width, in the short-side direction, of the block) in the short-side direction of each block (in this case, in both the vertical and horizontal directions on the screen using the two block groups) is detected. Since the signals of the outputs OUTY and OUTX are subjected to external light removal, i.e., consist of only signal light from the illumination light source, any bright point with a predetermined signal level or higher and a predetermined size or less can be considered as a Purkinje image, and when such a signal is detected, the approach of the eye can be determined. Furthermore, since the size of the bright point is detected in two directions, a discrimination result with higher precision can be obtained.

With the above-mentioned arrangement, since low power consumption is attained, a detecting operation for a long period of time including an all-time detecting operation can be realized even when the present invention is applied to, e.g., a camera using a power supply such as a battery with a limited capacity. In addition, since a reliable operation can be expected, the device of the present invention can serve as important switches such as a main switch, a distance measurement operation start/end switch, and the like in, e.g., a camera.

In each of the embodiments, the image sensor unit of image pickup means comprises an area sensor with a nondestructive readout photoelectric conversion element structure, but may comprise image sensors with other structures such as a CCD, a MOS sensor, a photodiode array, a sensor with another nondestructive readout photoelectric conversion element structure having a different circuit arrangement, or the like. However, in consideration of signals in units of blocks, easy acquisition of the maximum luminance value in each block, the operation power supply voltage, and the like, optical charge accumulation type sensors are preferable, and of these sensors, a sensor with a nondestructive readout photoelectric conversion element structure is more preferable.

The accumulation type sensor is suitable for the present invention since it does not require any consumption power in photoelectric conversion of signals or the accumulation operation itself of a charge. In addition, a sensor with a MOS structure such as a nondestructive readout photoelectric conversion element has a higher degree of freedom in accessibility to pixels than that of a CCD which is based on sequential transfer.

In each of the above embodiments, the number of illumination light sources is two for the sake of simplicity. Of course, three or more light sources may be used. In this case, the number of light sources, which are turned on concurrently, is not limited to one.

As described above, the device of the present invention comprises light-receiving means which consists of a plurality of pixels, and receives a reflected image generated by an observer's eye, the light-receiving means is divided into a plurality of regions each constituted by a plurality of pixels, and each of the divided regions outputs one luminance value. In this manner, since the information amount to be processed can be greatly reduced from an amount corresponding to the number of pixels to an amount corresponding to the number of regions while assuring a certain resolution of the light-receiving means, high-speed processing can be realized. In addition, processing can be attained even by a small-scale processing circuit, and the consumption of power of the processing circuit can be saved.

Furthermore, since the luminance value output from each region is a maximum value of the luminance values of a plurality of pixels, the luminance value can be easily discriminated.

Since the light-receiving means is divided into stripe-shaped regions extending in the first direction, a certain resolution of the luminance distribution in the first direction can be assured without increasing the number of regions.

Since the light-receiving means has first stripe-shaped regions in the first direction and second stripe-shaped regions in the second direction, and each first region and each second region have an overlapping portion, required resolutions of the luminance distributions in two directions can be assured without increasing the number of regions. For this reason, even when a small-scale processing circuit is used, high-resolution eye ball detection free from operation errors can be realized, and the consumption of power of the processing circuit can be saved.

Since the eye ball detecting device has a plurality of light projection means each for generating a reflected image on an observer's eye, and the eye ball detection is performed while switching the light projection means, detection errors caused by, e.g., an eclipse due to the eye lid, which may occur when only one light projection means is used, can be eliminated.

On the other hand, since the eye ball detecting device comprises light-receiving means which consists of a plurality of pixels and receives a reflected image generated by an observer's eye, timer means, and control means for repetitively controlling eye ball detection at predetermined time intervals measured by the timer means, the eye ball detecting operation can be performed intermittently. For this reason, since the detection is repeated a plurality of number of times, detection precision can be improved, and the consumption of power of the eye ball detecting device can be reduced.

What is claimed is:

1. An eye ball detecting device comprising:

light-receiving means for receiving light beams from an eye ball, said light-receiving means setting a plurality of regions thereon and outputting a maximum luminance value in each of said regions; and determination means for determining an approach of the eye ball when there is a value exceeding a predetermined level from among the outputs of the maximum luminance values in each of said regions output by said light-receiving means.

2. An eye ball detecting device according to claim 1, wherein said regions are set in a stripe pattern in a first direction of said light-receiving means.

3. An eye ball detecting device according to claim 1, wherein said regions have first regions set in a stripe pattern in a first direction of said light-receiving means and second regions set in a stripe pattern in a second direction of said light-receiving means, and said first and second regions have an overlapping portion.

4. An eye ball detecting device according to claim 1, further comprising:

light projection means for projecting light onto the eye ball of the user to generate the reflected light from said eye ball.

5. An eye ball detecting device according to claim 4, wherein said light projection means comprises a plurality of light projection elements, and switches said light projection elements on the basis of an output from said light-receiving means.

6. An apparatus having an eye ball detecting device, said apparatus comprising:

light-receiving means comprising a light receiving element for receiving light beams from an operator or a person to be examined and a plurality of regions, each of which are comprised of a plurality of pixels, said light-receiving means outputting maximum luminance values in each of said regions; and determination means for determining the approach of the eye ball of the operator or the person to be examined when there is a value exceeding a predetermined level from among the outputs of the maximum luminance values in each of said regions output by said light-receiving means.

7. An apparatus according to claim 6, further comprising:

light projection means for projecting light onto the eye ball of the user to generate the light reflected from said eye ball.

8. An apparatus according to claim 7, wherein said light projection means comprises a plurality of light projection elements, and switches said light projection elements on the basis of an output from said light-receiving means.

9. An eye ball detecting device, comprising:

a light receiving structure which includes a light receiving element for receiving a light beam from an operator or a person to be examined and a plurality of areas, each of which are comprised of a plurality of pixels, said light receiving structure outputting maximum luminance values in each of said regions; and a determination circuit which determines an approach of the eye ball of the operator or the person to be examined when there is a value exceeding a predetermined level among the outputs of the maximum luminance values in each of said regions output by said light receiving means.

10. An eye ball detecting device comprising:

a light projection structure which projects light to an eye ball of a user;

light-receiving means for receiving light beams from the eve ball, said light-receiving means setting a plurality of regions thereon and outputting a maximum luminance value in each of said regions;

determination means for determining an approach of the eye ball when there is a value exceeding a predetermined level from among the outputs of the maximum luminance values in each of said regions output by said light-receiving means;

a timer; and a control circuit which causes said light projection structure to repeat the light projection to the eye ball at a predetermined time interval measured by said timer.

* * * * *

UNITED STATES PATENT AND TRADEMARK OFFICE
CERTIFICATE OF CORRECTION

PATENT NO. : 5,892,985

DATED : April 6, 1999

INVENTOR(S) : Shinichi MATSUYAMA

It is certified that error appears in the above-identified patent and that said Letters Patent is hereby corrected as shown below:

ON THE COVER PAGE:

AT [57] Abstract:

Line 4, "examined," should read --examined.--.

Signed and Sealed this

Twenty-fourth Day of October, 2000

Attest:

Q. TODD DICKINSON

Attesting Officer

Director of Patents and Trademarks